United States Patent [19]
Tsuchiya et al.

[11] Patent Number: 5,475,766
[45] Date of Patent: Dec. 12, 1995

[54] PATTERN INSPECTION APPARATUS WITH CORNER ROUNDING OF REFERENCE PATTERN DATA

[75] Inventors: Hideo Tsuchiya; Toshiyuki Watanabe; Masao Takanashi; Masayuki Hideshima, all of Tokyo, Japan

[73] Assignee: Kabushiki Kaisha Toshiba, Kawasaki, Japan

[21] Appl. No.: 941,197

[22] Filed: Sep. 4, 1992

[30] Foreign Application Priority Data

Sep. 5, 1991 [JP] Japan ................................. 3-226074
Jan. 23, 1992 [JP] Japan ................................. 4-010050
Jan. 23, 1992 [JP] Japan ................................. 4-010051

[51] Int. Cl.$^6$ ............................... G06K 9/00; G06T 5/00
[52] U.S. Cl. ........................... 382/144; 382/199; 382/266; 348/126
[58] Field of Search ................................. 382/8, 48, 25, 382/22; 348/87, 126, 133

[56] References Cited

U.S. PATENT DOCUMENTS

| | | | |
|---|---|---|---|
| 4,300,122 | 11/1981 | McMahon | 382/22 |
| 4,442,542 | 4/1984 | Lin et al. | 382/8 |
| 4,479,145 | 10/1984 | Azuma et al. | 382/8 |
| 4,962,541 | 10/1990 | Doi et al. | 382/8 |
| 5,185,812 | 2/1993 | Yamashita et al. | 382/8 |
| 5,222,159 | 6/1993 | Kawamura et al. | 382/48 |

FOREIGN PATENT DOCUMENTS 1-45735 10/1989 Japan .
3-29178 4/1991 Japan .

Primary Examiner—Joseph Mancuso
Assistant Examiner—Larry J. Prikockis
Attorney, Agent, or Firm—Oblon, Spivak, McClelland, Maier & Neustadt

[57] ABSTRACT

A pattern inspection apparatus for comparing/collating a test target pattern with a corresponding design pattern to detect the presence/absence of a defect which is present in the test target pattern includes a bit pattern generating circuit for developing the data of the design pattern into bits, a corner pattern detector for scanning a corner pattern detection window having a predetermined range with respect to reference pattern data as a reference of a pattern obtained by bit development performed by the bit pattern generating circuit to extract a contour pattern, and detecting a corner pattern to be subjected to corner rounding processing on the basis of the extracted contour pattern, a memory for storing predetermined change information corresponding to the corner detected by the corner pattern detector, a graphic pattern synthesizing circuit for changing a graphic pattern in accordance with the information in the memory, and a comparing circuit for comparing reference pattern data, obtained by rounding processing performed on the basis of the reference pattern data and the feature of the corresponding pattern, with test pattern data obtained from the test target pattern, and further includes a pattern correcting circuit constituted by an excessive rounding detector for detecting and correcting an inadequate excessive rounding operation, and a pattern changing circuit for changing the pattern data in accordance with the excessive rounding detection result.

14 Claims, 31 Drawing Sheets

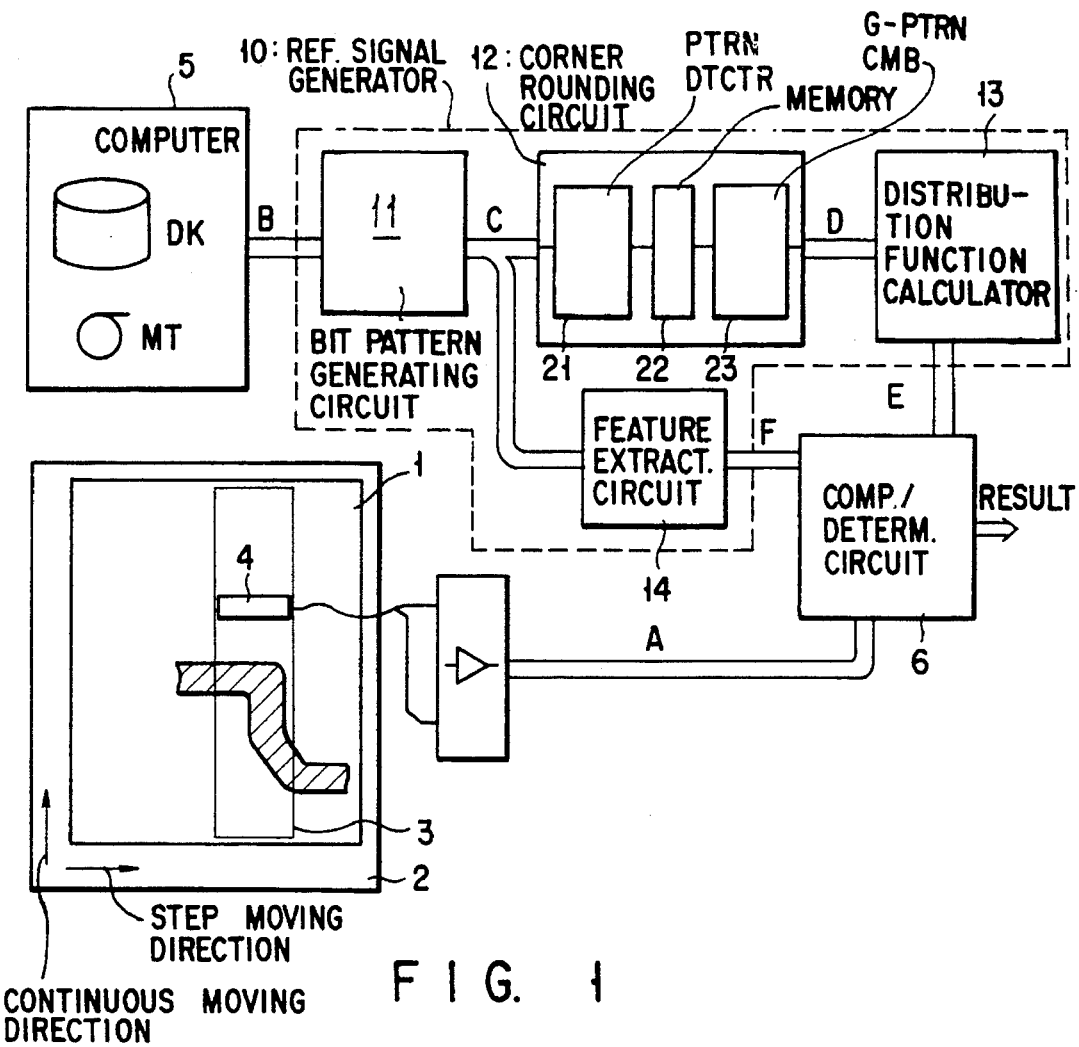
F I G. 1
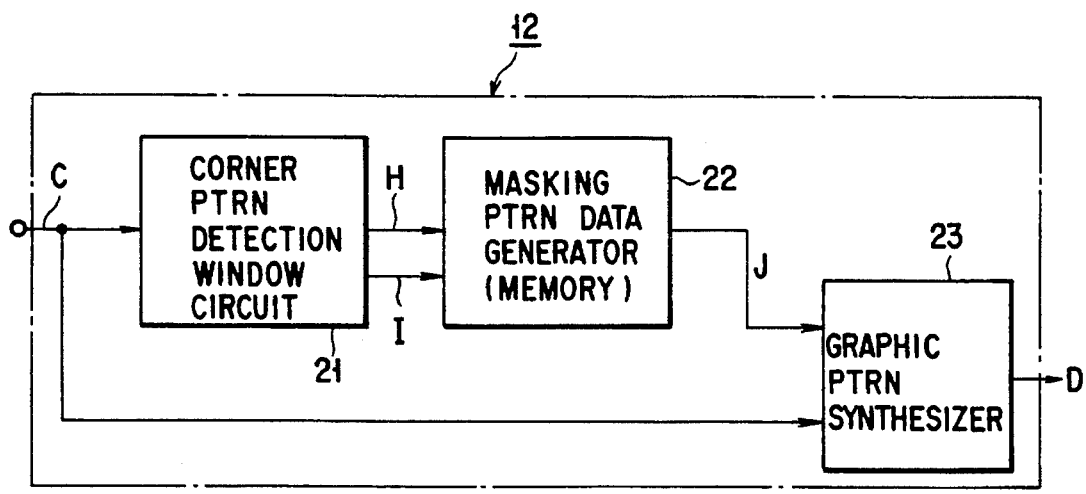
F I G. 2

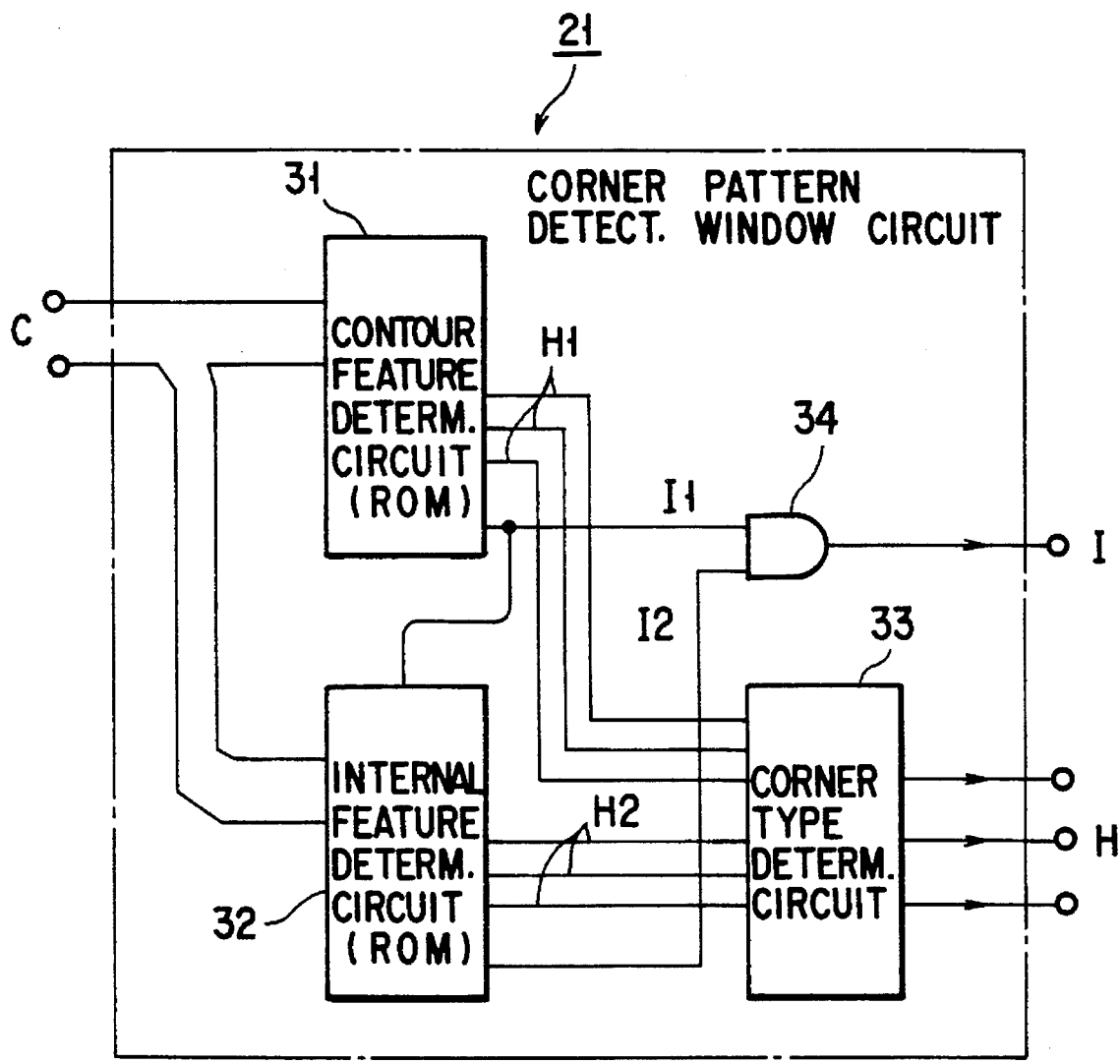
F I G. 5

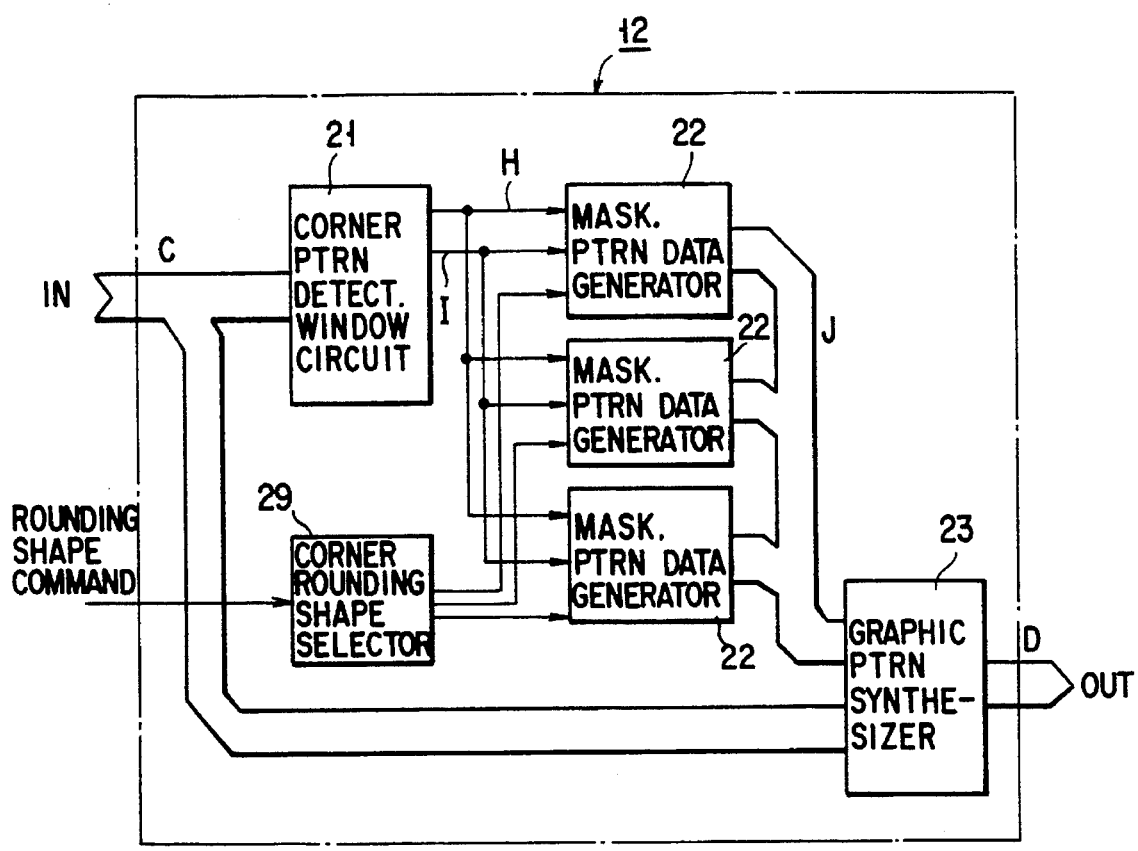
FIG. 9
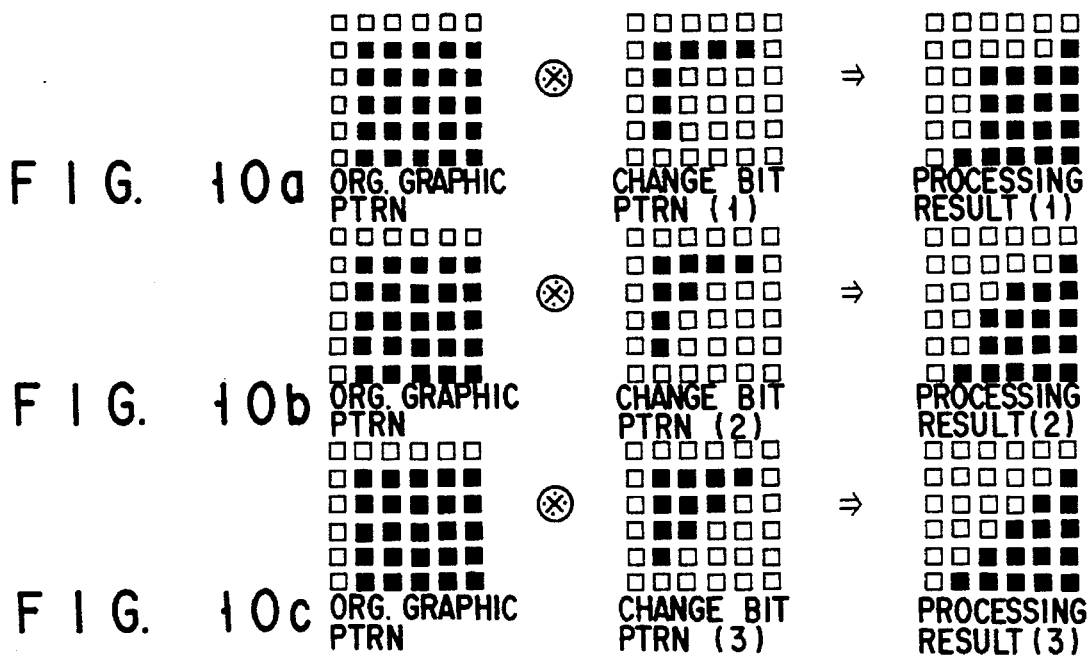
FIG. 10a
FIG. 10b
FIG. 10c

ORG. GRAPHIC PTRN

MASK. PTRN

OUTPUT OBTAINED BY SYNTHE-
SIZING GRAPHIC PTRN

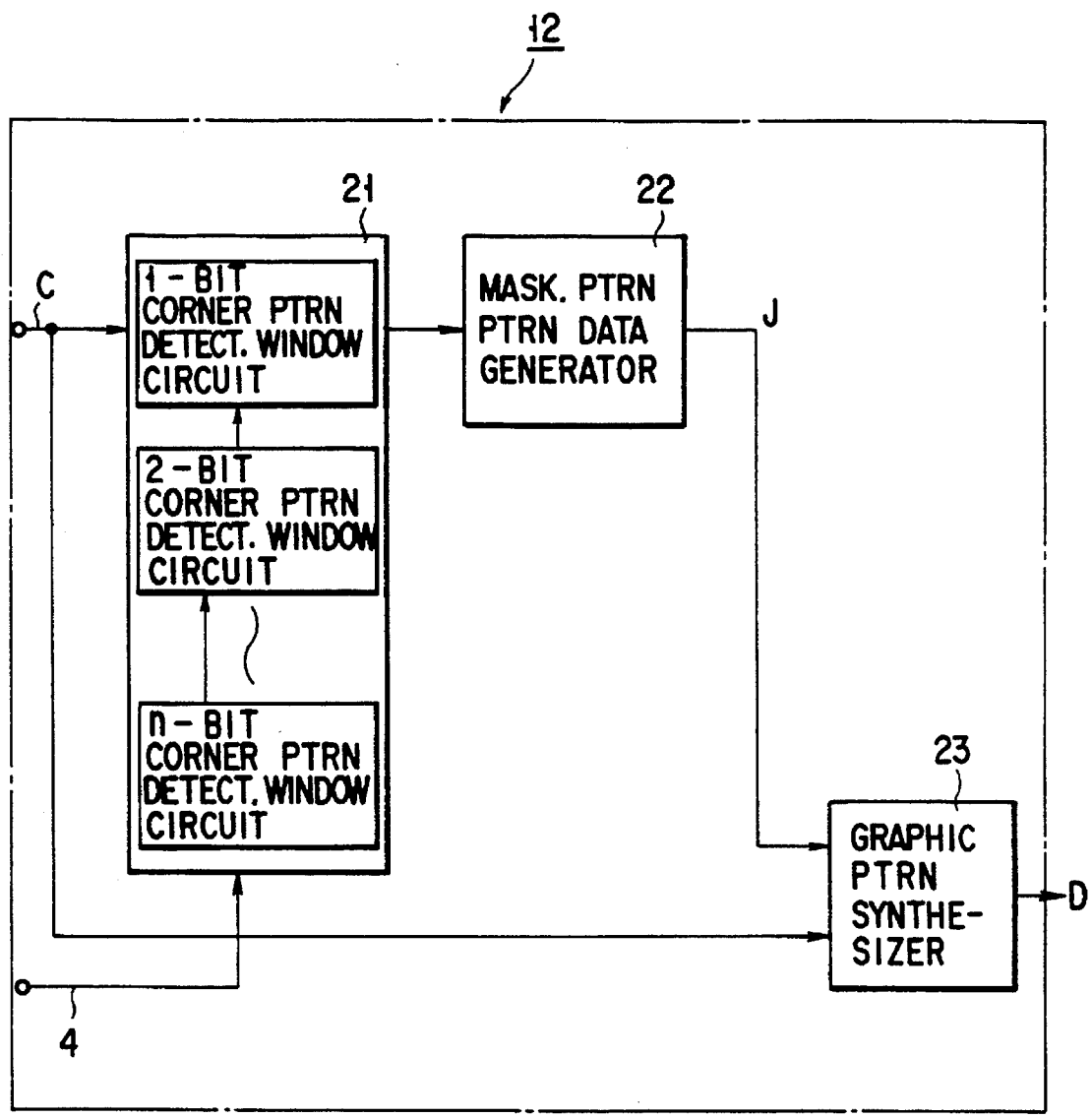
F I G. 15

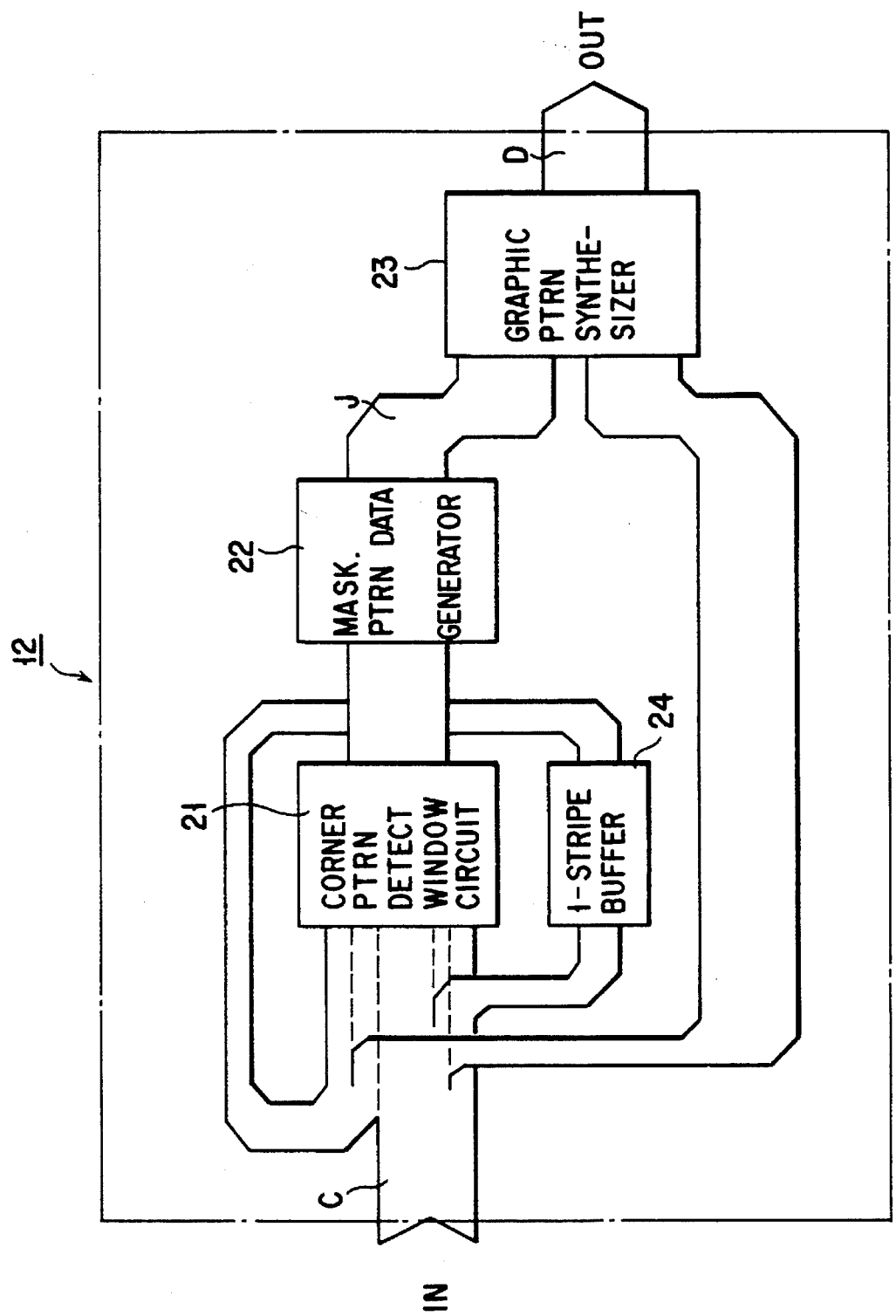
F I G. 17

(1) CORNER PATTERN DETECTION

◌　STRIPE DATA IS "WHITE"

☐　STRIPE DATA IS "BLACK"

☒　STRIPE DATA MAY BE "WHITE" OR "BLACK"

(2) FUNCTION OF MASKING PATTERN

☒　INVERT "BLACK" INTO "WHITE"

○　INVERT "WHITE" INTO "BLACK"

(3) DETECTION/CHANGE OF MASKING PATTERN

△　MASKING PATTERN IS ABSENT

△　MASKING PATTERN IS PRESENT

△　MASKING PATTERN MAY BE PRESENT OR ABSENT

▲　MASKING PATTERN IS PRESENT AND CANCEL IT (4) FUNCTION OF CORNER-ROUNDED PATTERN CORRECTING CIRCUIT

■　CANCEL "☒"

●　CANCEL "○"

FIG. 21

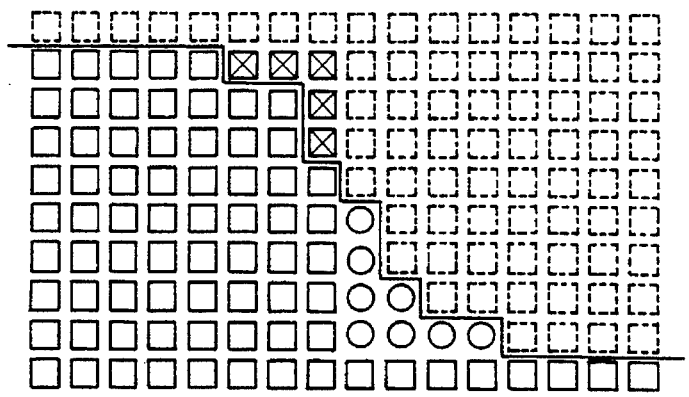
FIG. 23a    8-BIT STEP
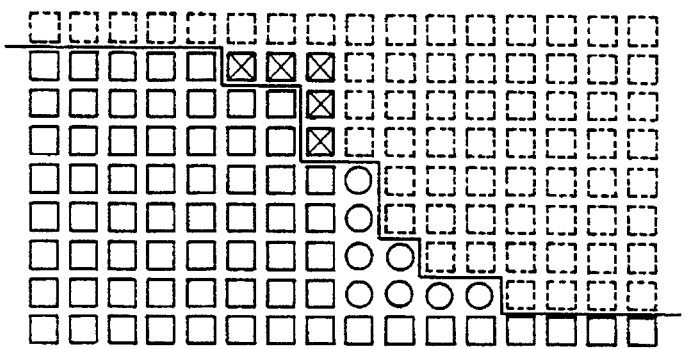
FIG. 23b    7-BIT STEP
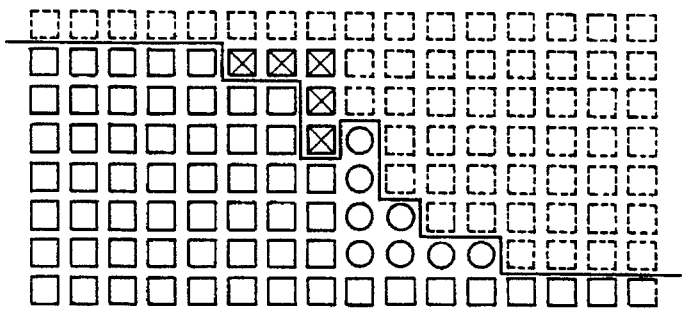
FIG. 23c    6-BIT STEP
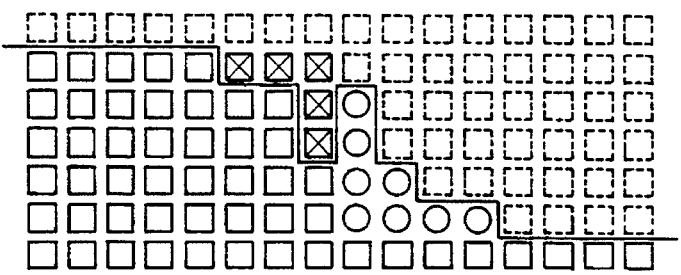
FIG. 23d    5-BIT STEP

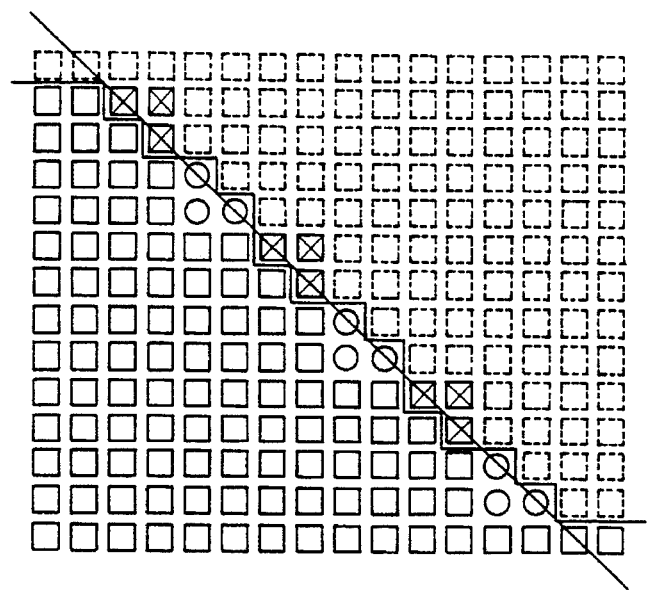
F I G. 24
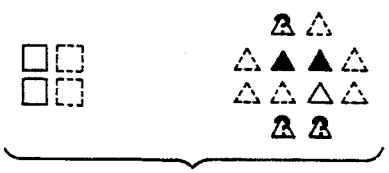
F I G. 25a
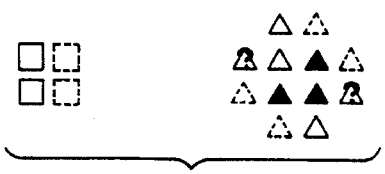
F I G. 25b
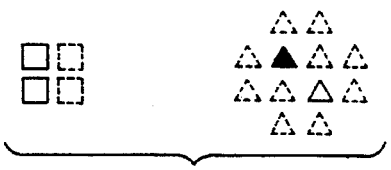
F I G. 25c
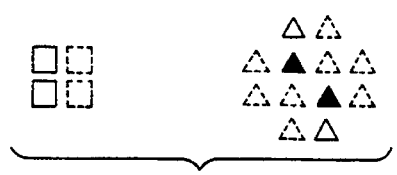
F I G. 25d
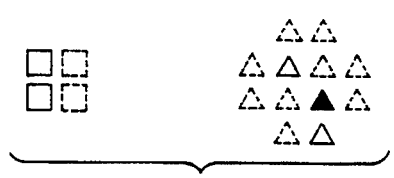
F I G. 25e
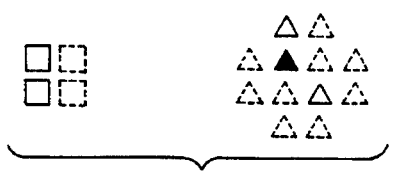
F I G. 25f

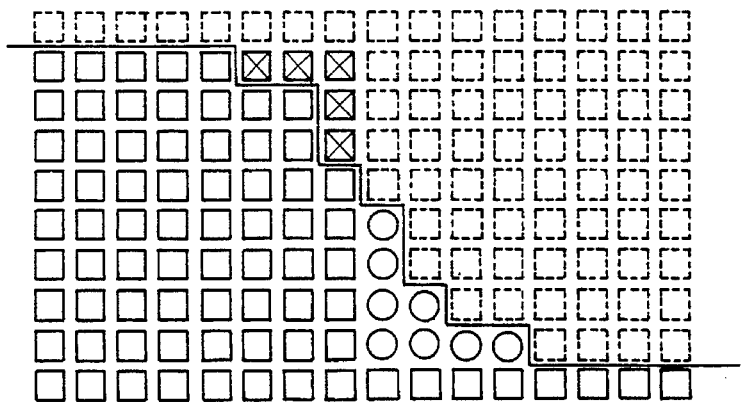
F I G. 26a    8-BIT STEP
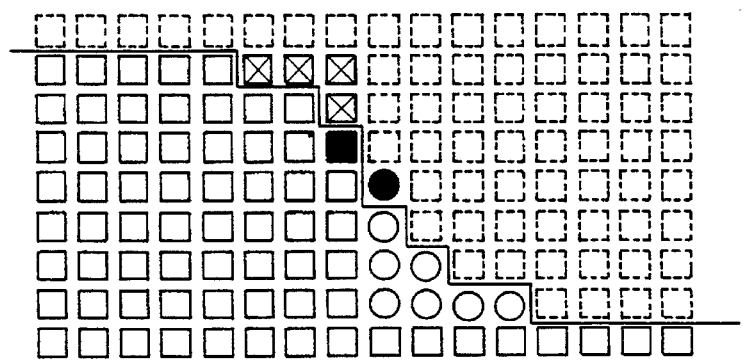
F I G. 26b    7-BIT STEP
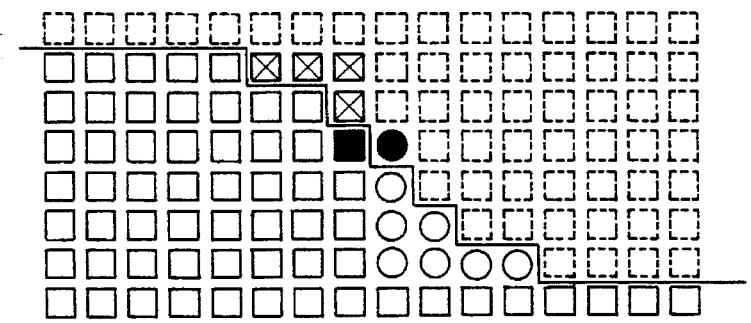
F I G. 26c    6-BIT STEP
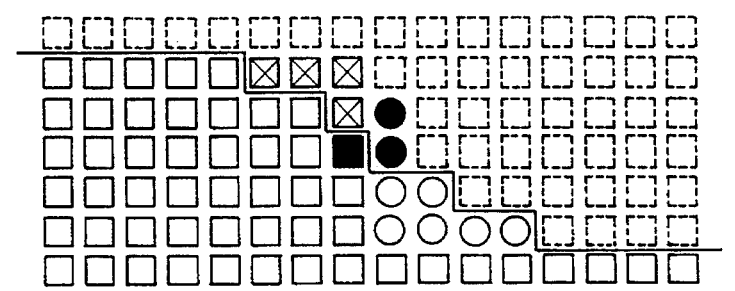
F I G. 26d    5-BIT STEP

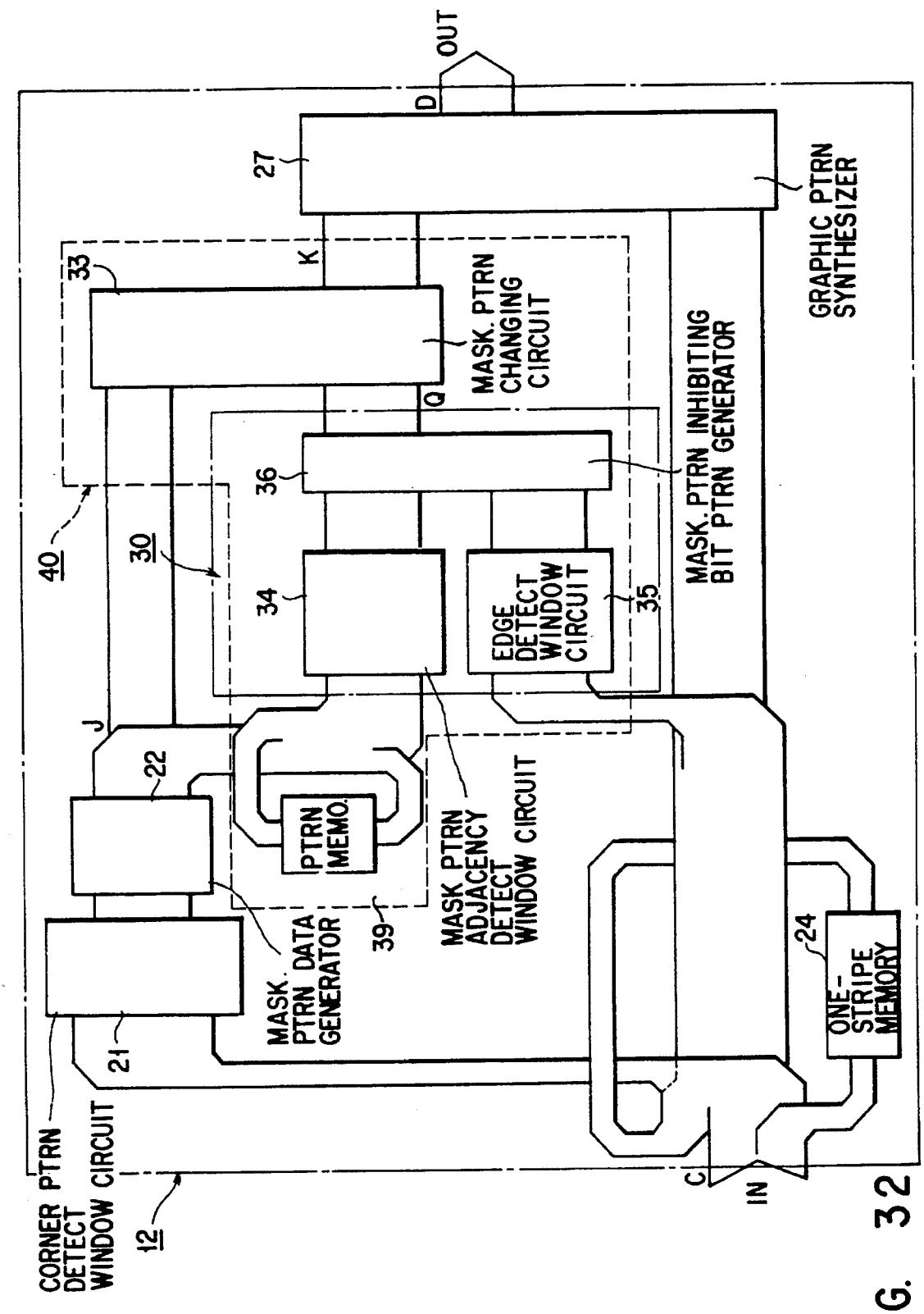
F I G. 32

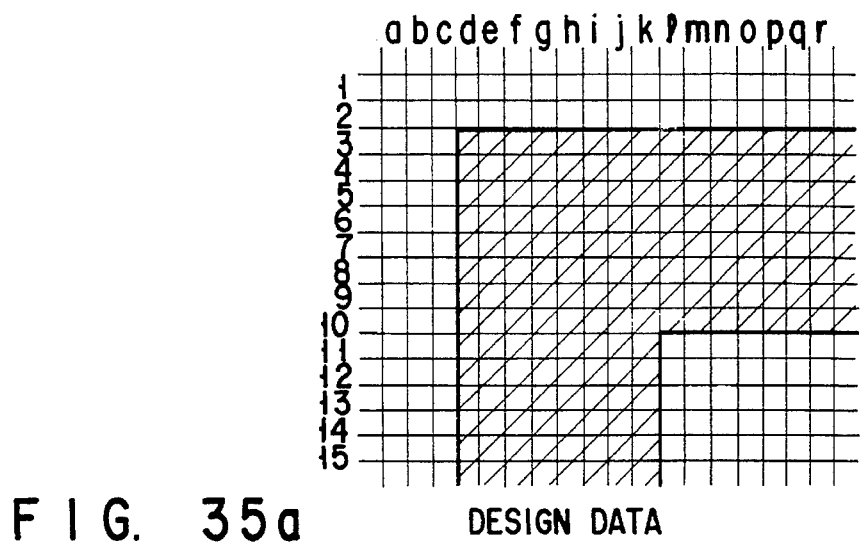
FIG. 35a  DESIGN DATA
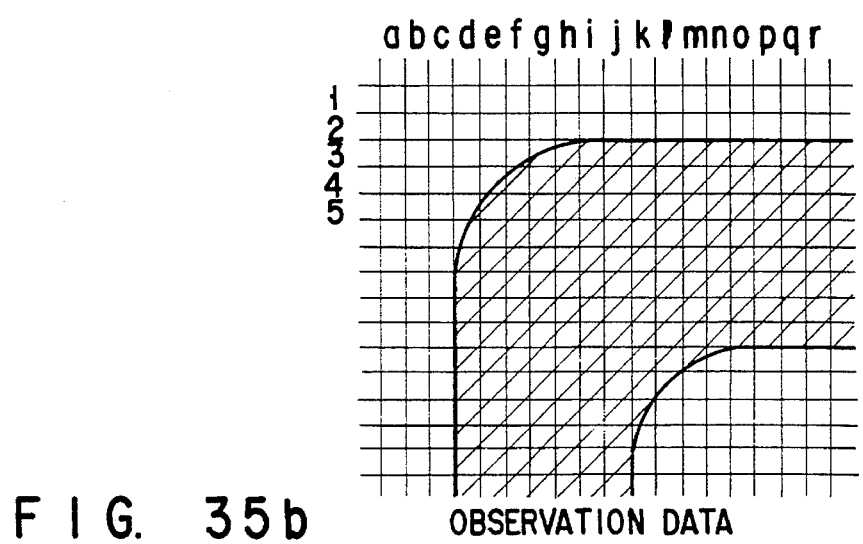
FIG. 35b  OBSERVATION DATA
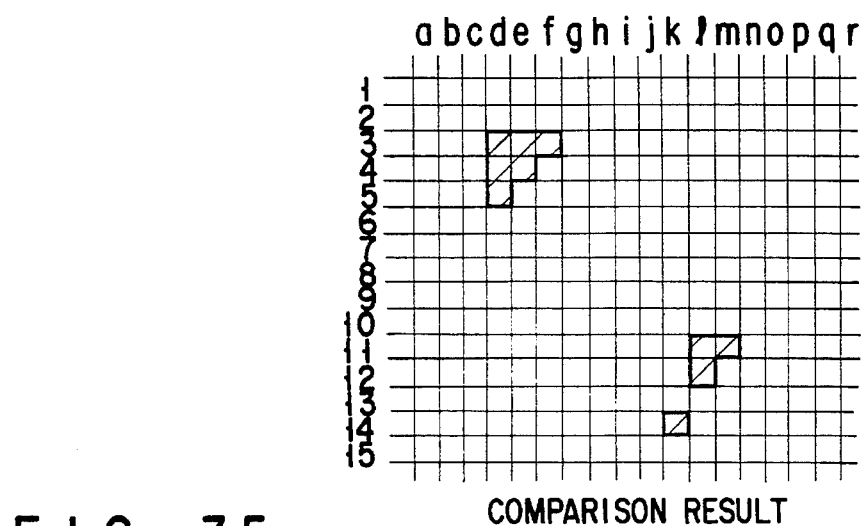
COMPARISON RESULT
FIG. 35c
(PRIOR ART)

PATTERN INSPECTION APPARATUS WITH CORNER ROUNDING OF REFERENCE PATTERN DATA

BACKGROUND OF THE INVENTION

1. Field of the Invention

The present invention relates to a pattern inspection apparatus for detecting a pattern defect in a reticle or a mask used for the manufacture of a semiconductor integrated circuit or a liquid crystal display apparatus and, more particularly, to a pattern inspection apparatus having a function of rounding (definition: rounding corners) reference pattern data.

2. Description of the Related Art

In the manufacture of a semiconductor integrated circuit, if a defect such as a pattern disconnection exists in a photomask used for pattern transfer, a desired semiconductor element cannot be obtained, resulting in a reduction in yield. A pattern inspection apparatus, therefore, has been used to inspect a pattern defect or the like in a photomask formed by an electron beam drawing unit and so on. This apparatus is designed to detect an optical signal corresponding to a pattern formed on a photomask by radiating light on the mask and compare/collate the detected signal with a reference signal obtained from design data used to form the pattern on the mask, thereby inspecting the presence/absence of a pattern defect in the mask and the validity of the pattern.

FIG. 33 is a block diagram showing a schematic arrangement of a conventional pattern inspection apparatus. In this apparatus, a table 2 on which a photomask 1 is placed is continuously moved in the X or Y direction to perform inspecting in units of stripes 3. The table 2 is then moved in a direction perpendicular to the continuously moving direction by an amount corresponding to the stripe width, and repeatedly performs inspecting in units of stripes, thereby inspecting the entire pattern formation region on the photomask 1.

In this stripe inspecting testing, an optical signal corresponding to the pattern formed on the photomask 1 is detected by an optical sensor 4 to obtain observation value A, while design data B used to form the pattern on the photomask 1 is read out from a computer 5 to prepare bit pattern data C' shown in FIG. 34 in a bit pattern generating circuit 11 of a reference signal generator 10, and reference data C corresponding to each pixel of the observation data A is prepared. Both the resultant signals are compared/collated with each other at each measurement position of the table 2. The above-described processing is performed while the table 2 is continuously moved at a constant speed.

In the conventional inspection apparatus, the reference data C prepared from the design data B forms a very accurate image as compared with the image formed by the observation data A. For this reason, when the pattern based on the reference data C is compared with the actual pattern, their difference is increased, especially at corner portions of the patterns, and a defect may be determined. More specifically, as shown in FIGS. 35a to 35c, the original graphic pattern (FIG. 35a) obtained by bit pattern development of design pattern data has a clear pattern edge and a clear corner shape. In contrast to this, both the pattern edge and corner shape exhibited by the observation data (FIG. 35b) picked up by the optical sensor 4 are blurred and rounded. If, therefore, they are simply compared with each other, as indicated by the comparison result (FIG. 35c), large errors are detected at portions corresponding to the corner and the edge, and a defect is determined.

In the actual manufacture of a mask, however, the corners of a pattern are usually rounded, and a certain degree of rounding has no influence on the electrical characteristics of a semiconductor integrated circuit. For this reason, it is preferable to proceed with a inspecting operation without determining such a rounded corner of a mask pattern as a defect.

In the apparatus shown in FIG. 33, in order to compensate for blurring based on the aperture characteristics of a lens, interference between adjacent pixels in a sensor, and the likes caused in an observation optical system, weighting/addition and multivalue conversion of the reference data C are performed by a point spread function in a distribution function calculator 13 to approximate the overall rounding (blurring) of the observation data A, thus obtaining reference data E. In addition, a feature extracting circuit 14 is used to extract a feature indicating whether a graphic pattern in an observation region white is being tested is a corner or a portion other than a corner, i.e., an entirely black pattern, an entirely while pattern, or an edge portion of a pattern, and an error threshold value F used for comparing/testing processing is updated that each feature so that a small difference in shape between patterns is not determined as a defect. This means that updating the threshold value F is effective in preventing the occurrence of false-defects especially at corner portions of a pattern.

The following problem, however, is posed in an apparatus of this type. In a mask pattern having a rounded corner, the threshold value range at the corner must be set to be broad in order to prevent the occurrence of a false-defect. If, however, the threshold value range is excessively widened, even a defect which is present near the corner and must be discriminated cannot be detected.

As described above, in the conventional pattern testing apparatus, since a corner of an actually manufactured mask pattern is generally rounded, even a portion which is not a defect (false-defect) is determined as a defect upon comparison between reference pattern data and pattern data to be inspected. In addition, if the threshold value range for comparison at the corner is excessively widened, a defect which is present near the corner cannot be detected.

SUMMARY OF THE INVENTION

It is an object of the present invention to provide a pattern inspection apparatus which can prevent the occurrence of a false-defect caused by a rounded corner, and can reliably detect a defect near a corner without determining a false-defect as a defect, thereby improving the pattern testing precision.

The gist of the present invention is that reference pattern data is compared with test pattern data upon performing rounding processing of a corner portion of the reference pattern data.

According to the present invention, there is provided a pattern inspection apparatus for comparing/collating test pattern data obtained from a test target pattern with design pattern data of the pattern to detect the presence/absence of a defect which is present in the test target pattern, comprising a bit pattern generating circuit for developing the design pattern data into bits, a corner pattern detector for scanning a corner pattern detection window with respect to reference pattern data obtained by the bit development to extract a contour pattern in the window, and detecting a corner pattern to be subjected to corner rounding processing on the basis of the extracted contour pattern, a masking pattern data generator for generating masking pattern data corresponding to the detected corner pattern, a graphic pattern synthesizer for synthesizing graphic pattern data (part of the reference pattern data) including the detected corner pattern with masking pattern data corresponding to the graphic pattern data (by, e.g., exclusive OR processing), thereby rounding a corner portion of the reference pattern data, and a comparing circuit for comparing the synthesized reference pattern data with the test pattern data.

According to the present invention, a reference pattern can be approximated to an actually formed test target pattern having a rounded corner by performing corner rounding processing with respect to reference pattern data obtained by performing bit development of design pattern data. Therefore, the present invention can prevent a false-defect caused by a rounded corner from being determined as a defect. In addition, since the threshold value range for comparison/ determination at a corner can be set to be narrower than that set in the conventional apparatus having a broad threshold value range at a corner, a defect near a corner can be reliably detected. Consequently, the pattern inspecting precision can be improved.

In addition, according to the present invention, since corner detection is performed on the basis of a contour portion of a corner pattern detection window, all the bits in the window need not be concerned. Therefore, the processing required for corner pattern detection can be simplified, and the time required therefor can be shortened. Furthermore, by inspecting not only a contour pattern but also an internal pattern, and performing a logical operation of the respective inspecting results, a corner to be subjected to rounding processing can be more accurately detected.

Furthermore, a pattern inspection apparatus of the present invention comprises an excessive rounding detector for scanning reference pattern data and corresponding masking pattern data to detect inadequate excessive rounding caused when corner rounding processing is performed with respect to a plurality of adjacent corners, and a masking pattern changing circuit for changing a masking pattern in accordance with a detection result obtained by the detector.

Since the present invention further includes the excessive rounding detector and the masking pattern changing circuit, the generation of reference pattern data which cannot be obtained in an actual reticle manufacturing process can be prevented, which data is generated when the distance between the respective corners to be rounded is close as compared with the size of a masking pattern. Therefore, defects even in more complicated patterns can be inspected with high precision.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing a schematic arrangement of a pattern testing apparatus according to the first and second embodiments of the present invention;

FIG. 2 is a block diagram showing the arrangement of a corner rounding circuit used in the first embodiment of the present invention;

FIG. 5 is a block diagram showing the arrangement of a corner pattern detector;

FIG. 9 is a block diagram showing the arrangement of a corner rounding circuit used in the second embodiment of the present invention;

FIGS. 10a, 10b, and 10c are views, each showing a change in optimal pattern of each masking pattern;

FIG. 15 is a block diagram showing the arrangement of a main part of the fourth embodiment of the present invention;

FIG. 17 is a block diagram showing the arrangement of a main part of the fifth embodiment of the present invention;

FIG. 21 is a view for explaining symbols used for display processing;

FIGS. 23a to 23d are views showing examples of excessive rounding patterns to be corrected;

FIG. 24 is a view showing a case wherein phase inversion occurs;

FIGS. 25a to 25f are views showing masking patterns and stripe patterns;

FIGS. 26a to 26d are views showing examples of patterns obtained by correcting the patterns shown in FIGS. 23a to 23d;

FIG. 32 is a block diagram showing the arrangement of the main part of the eighth embodiment of the present invention;

FIGS. 35a to 35c are views showing design data, observation data, and comparison data, each of which has undergone bit pattern development.

DETAILED DESCRIPTION OF THE PREFERRED EMBODIMENT

(First Embodiment)

Figure 33:
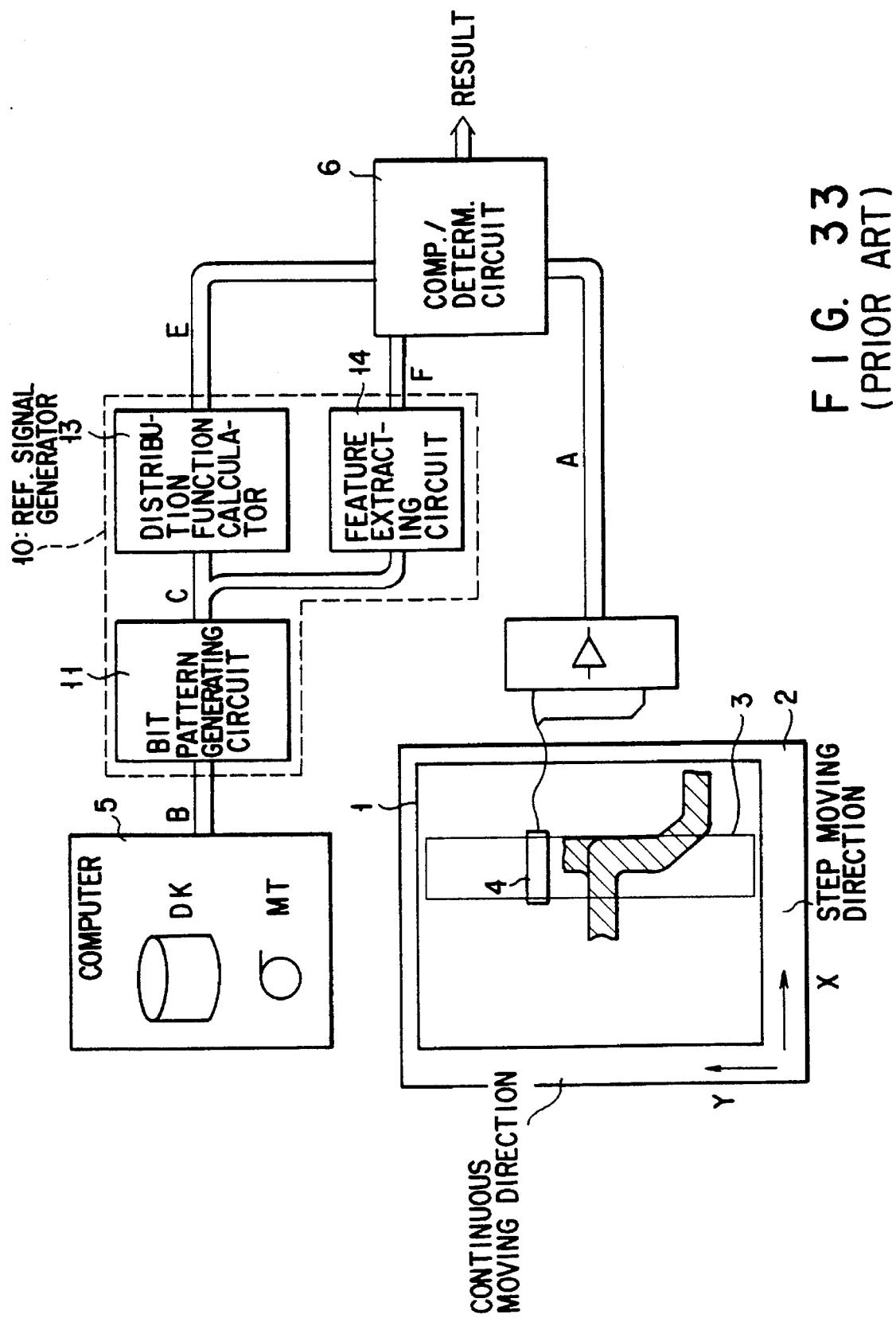
FIG. 33 is a block diagram showing a schematic arrangement of a conventional pattern testing apparatus.
Figure 34:
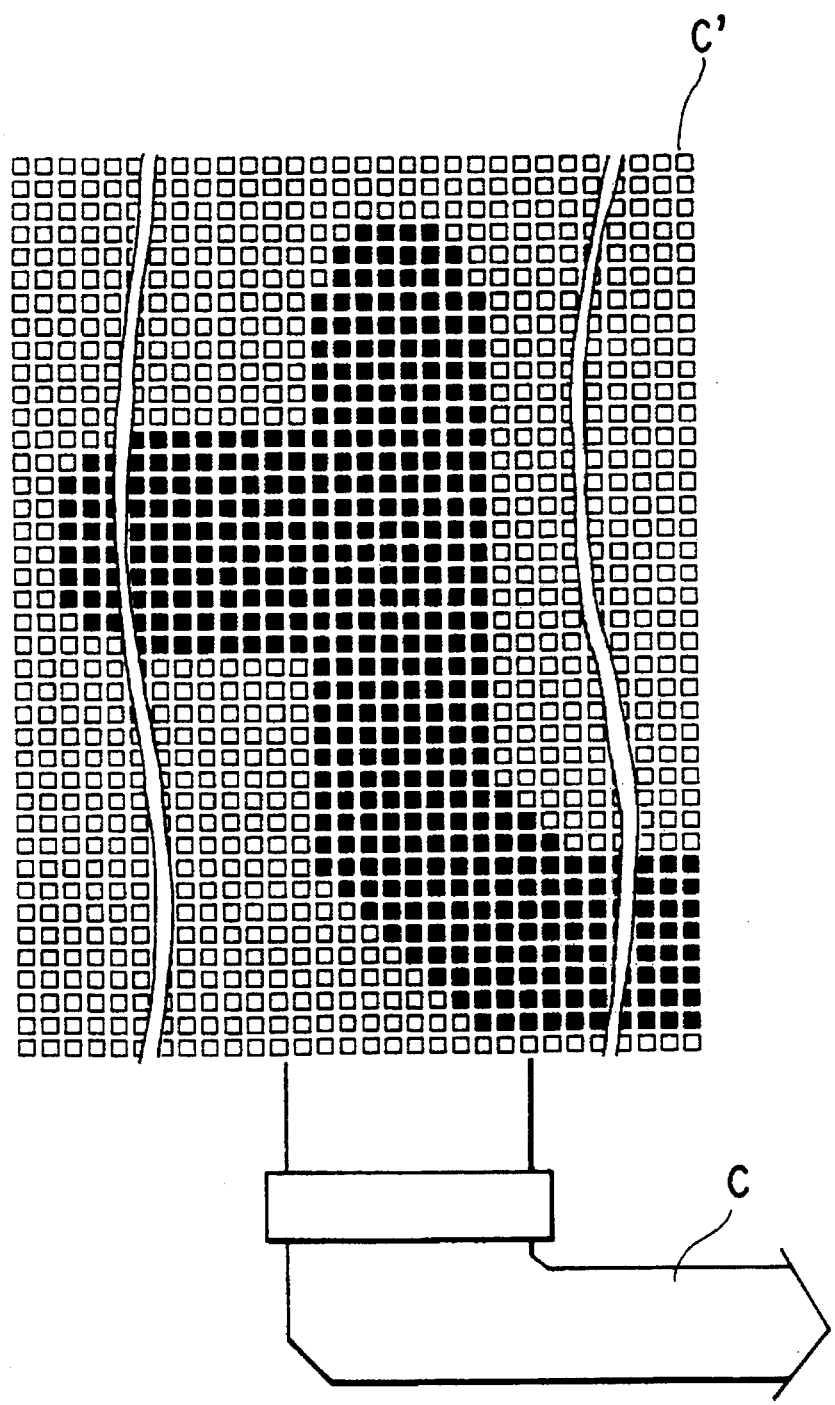
FIG. 34 is a view showing a bit pattern developed from designed data.

FIG. 1 is a block diagram showing a schematic arrangement of a pattern inspection testing apparatus according to the first and second embodiments of the present invention. The basic characteristic feature of the arrangement of this apparatus is that a corner rounding circuit 12 is added to a reference signal generator 10 in the conventional apparatus shown in FIG. 33.

Figure 8A:
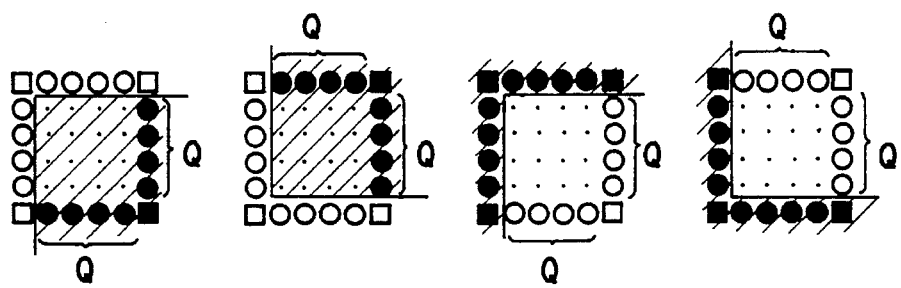
FIGS. 8a and 8b are views for explaining bit determination processing for a contour.
Figure 8B:
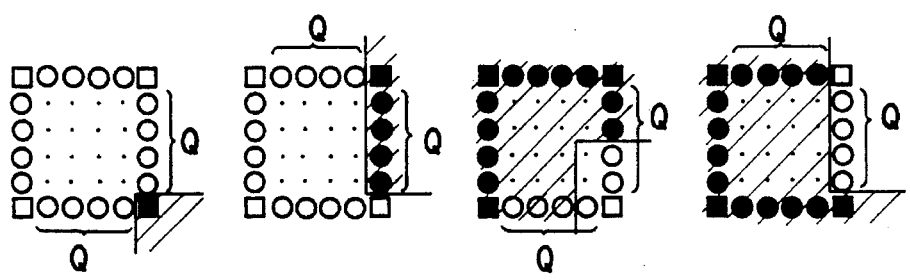

Referring to FIG. 1, design pattern data B supplied from a computer 5 is developed into bit pattern data as reference pattern data C by a bit pattern generating circuit 11. The data C is then supplied to the corner rounding circuit 12 and a feature extracting circuit 14. The corner rounding circuit 12 performs corner rounding processing (to be described later) on the basis of the reference pattern data C, and subsequently supplies a rounding result D to a distribution function calculator 13. As the output from the bit pattern generating circuit 11, two-dimensional bit pattern data as shown in FIGS. 8a and 8b are supplied to the corner rounding circuit 12 and the feature extracting circuit 14 as stripe data. The corner rounding circuit 12 has a pattern detecting function, a memory function, and a graphic pattern synthesizing function (each of which will be described later). The circuit 12 receives this stripe data C as input data. If there is a pattern corresponding to a corner having a preset constituent bit count, the corner pattern is replaced with pattern data D having a rounded corner (i.e., rounding processing). The corner rounding circuit 12 then outputs the pattern data D to the distribution function calculator 13.

The distribution function calculator 13 performs distribution processing with respect to the pattern data D supplied from the corner rounding circuit 12 by performing a predetermined function calculation, and supplies the resultant data as an output E to a comparing/determining circuit 6. Meanwhile, test pattern data A obtained from a pattern to be tested is supplied to the comparing/determining circuit 6, and the output E of the corner rounding circuit 12 is compared with the test pattern data A. The feature extracting circuit 14 performs feature extraction by discriminating whether a graphic pattern in an observation region, which is being tested, is a corner or a portion other than a corner, e.g., an entirely black pattern, an entirely white pattern, or an edge portion of a pattern, and updates an error threshold value F, used for comparing/testing processing, for each feature.

The corner rounding circuit 12 in the first embodiment, shown in FIG. 2, is constituted by a corner pattern detection window circuit 21, a masking pattern data generator 22 connected to the circuit 12 and having a data generating function or a memory function, and a graphic pattern synthesizer 23 connected to the circuit 22 and having a synthesizing function.

The corner pattern detection window circuit 21 operates a corner pattern detection template having a predetermined bit configuration, every time the reference pattern data C as stripe data is input to the circuit 21, thus detecting whether each input data includes a pattern whose corner is to be rounded. If the corner pattern detection window circuit 21 detects a pattern whose corner is to be rounded, the circuit 21 sets a graphic pattern code H indicating the coincidence-detected graphic pattern and a flag I indicating the coincidence with the feature, and supplies them to a masking pattern data generator 22. If the flag I is set in the corner pattern detection window 21, the masking pattern data generator 22 generates a masking pattern J corresponding to the graphic pattern code H output from the corner pattern detection window circuit 21. Note that these graphic codes H are discriminated depending on the direction of a corner of a pattern, whether a pattern is a concave or convex pattern, or the like. In addition, the masking pattern data generator 22 generates a bit pattern in which data "1 (:ON)" are set in an original graphic pattern prior to corner rounding processing at the positions of bits to be subjected to black and white inversion, and data "0 (:OFF)" are set at other positions.

Figure 3A:
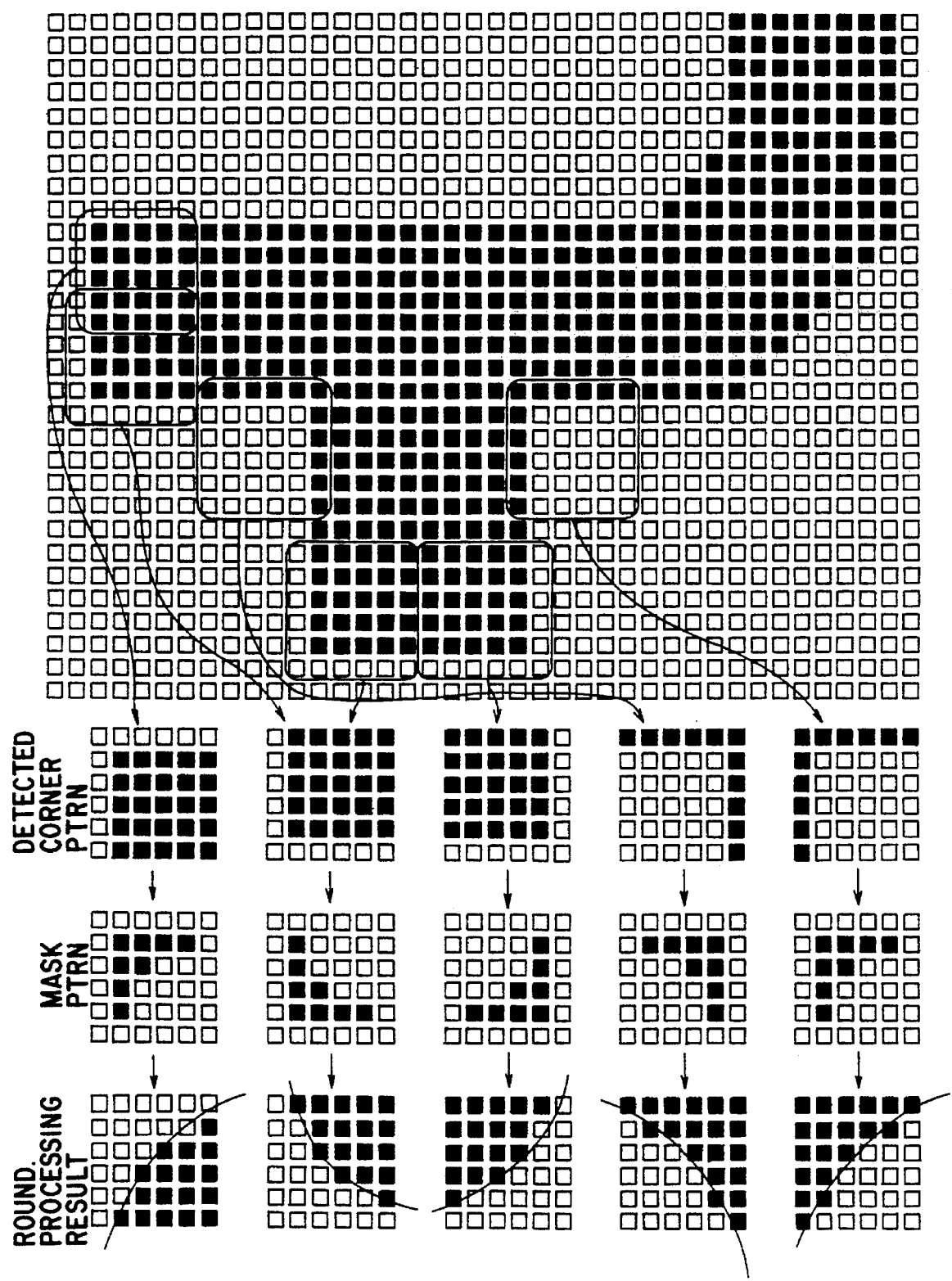
FIGS. 3a and 3b are views for explaining the respective data in corner rounding processing.
Figure 3B:
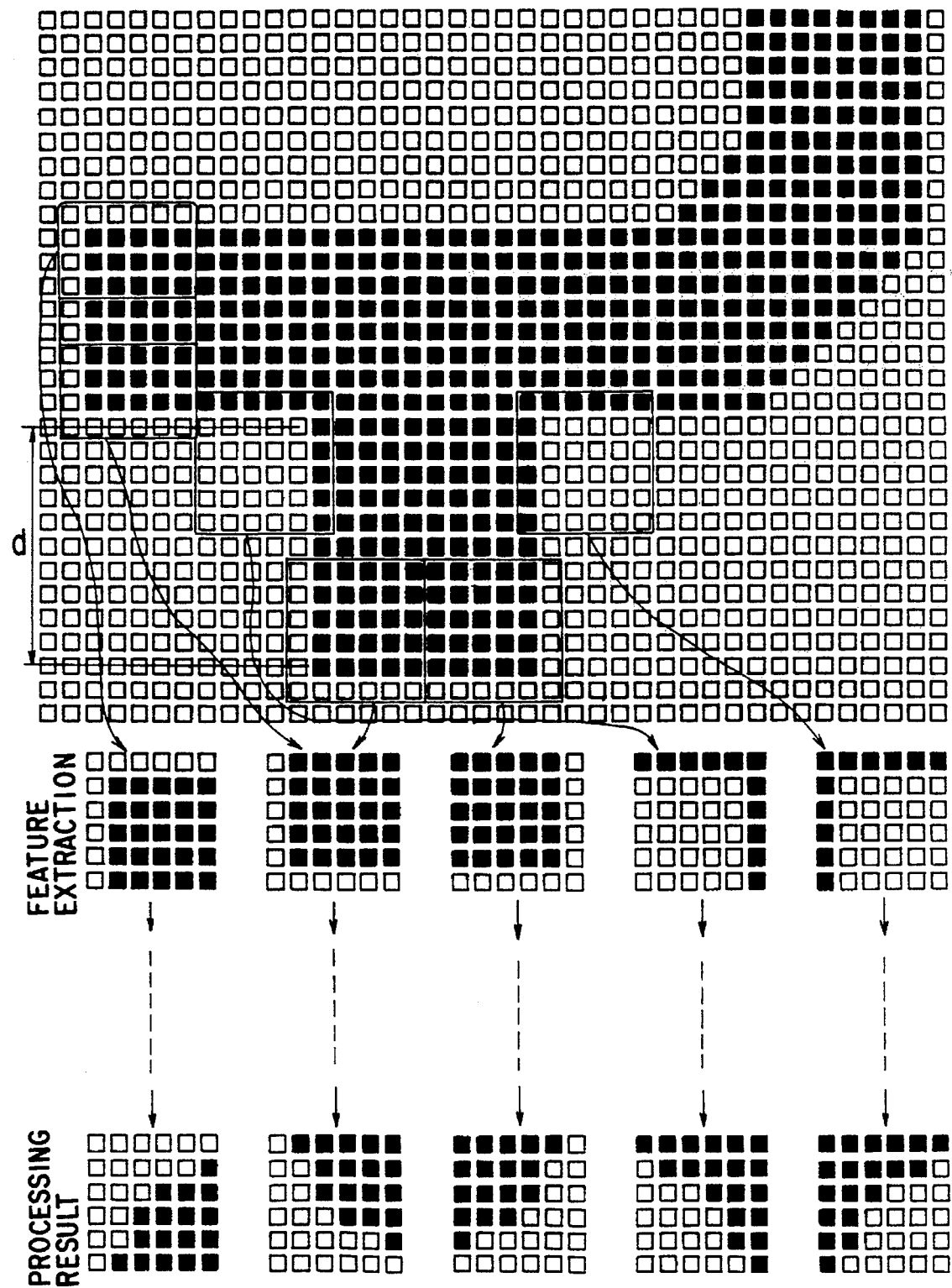
Figure 4:
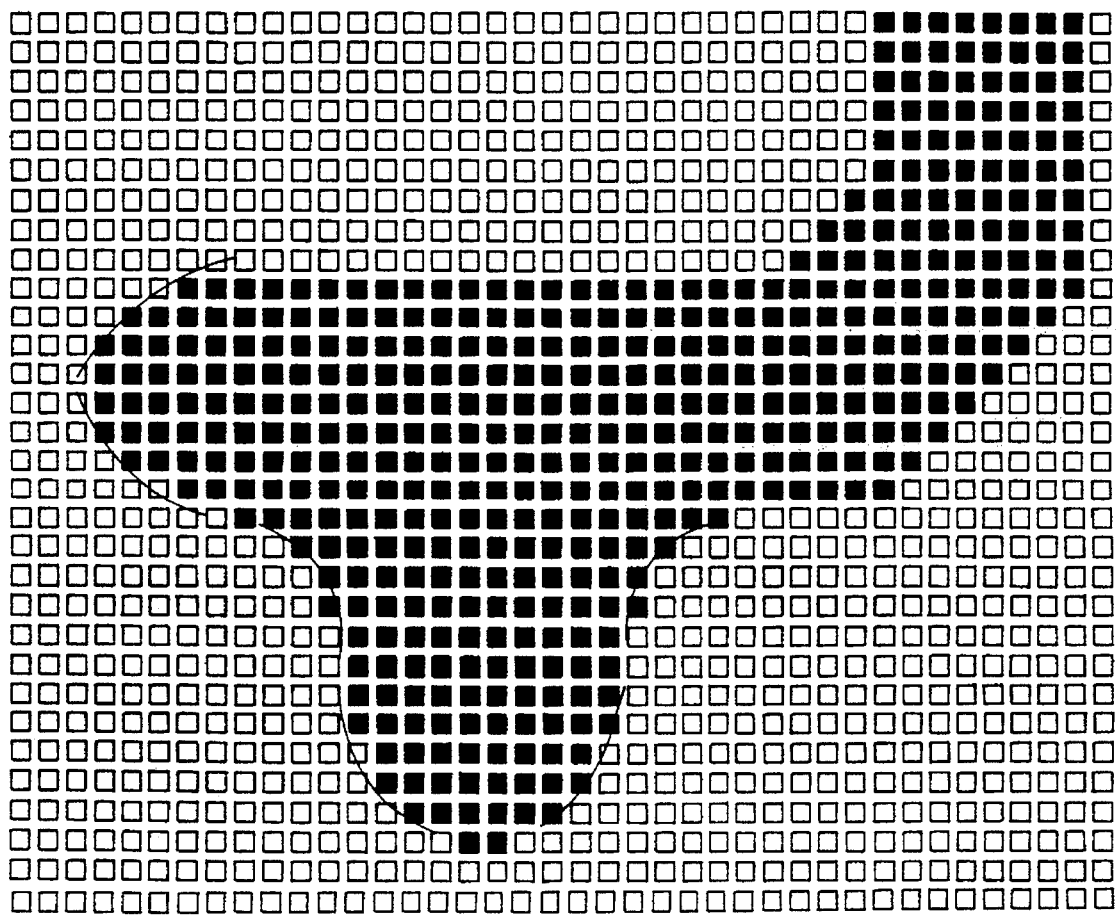
FIG. 4 is a view showing a result obtained by corner rounding processing of a bit pattern.

FIGS. 3a and 3b show corner patterns detected by the corner pattern detection window circuit 21 and masking patterns generated by the masking pattern data generator 22 which correspond to original graphic patterns. More specifically, the graphic pattern synthesizer 23 performs an exclusive OR operation between the corner patterns (i.e., the original graphic patterns) and the masking patterns (i.e., the change bit patterns), which patterns are shown at lower positions in FIG. 3a, in units of bits. That is, only bits of an original graphic pattern which correspond to "1"-level bits of a corresponding masking pattern are subjected to black and white inversion processing (exchange data "0" and data "1"). If, for example, an original graphic pattern is a convex corner pattern, the graphic pattern synthesizer 23 cuts off its convex corner. If it is a concave corner pattern, the circuit 23 serves to expand (fill up) its concave corner. FIG. 3b shows a scheme in which graphic processing of feature-extracted original graphic patterns are directly performed without using mask patterns generated by the masking pattern generator 22. This scheme indicates that a modification of the first embodiment designed to obtain a result by means of corner rounding processing can be realized. FIG. 4 shows an output pattern obtained by the above-described rounding processing.

FIG. 5 shows a detailed circuit arrangement of the corner pattern detection window circuit 21 for performing 4-bit rounding processing in accordance with the principle of the operation performed by the above-described constituent elements. The corner pattern detection window circuit 21 is constituted by a contour feature determining circuit 31, an internal feature determining circuit 32, a corner type determining circuit 33, and an AND gate 34. Note that the actual corner pattern detection window circuit 21 requires not only bits to be subjected to rounding processing but also peripheral bit pattern data extending from the target bits in all the directions by 1 bits. That is, when 4-bit rounding processing is to be performed, detection must be performed throughout a two-dimensional pattern of 6×6=36 bits.

In order to perform corner rounding processing with respect to a bit pattern having a large radius of curvature, it must be detected in advance that the curvature does not contradict a corner. That is, a corner pattern detection window circuit 21 having a large constituent bit count must be prepared. In addition, when corner pattern detection is to be performed with respect to a large bit configuration, detection of a corner pattern or detection of the directional feature of a corner need not be performed for all the bits in the corner detection window. That is, approximate determination can be performed by testing only the bits at a contour portion of the detection window.

Figure 6:
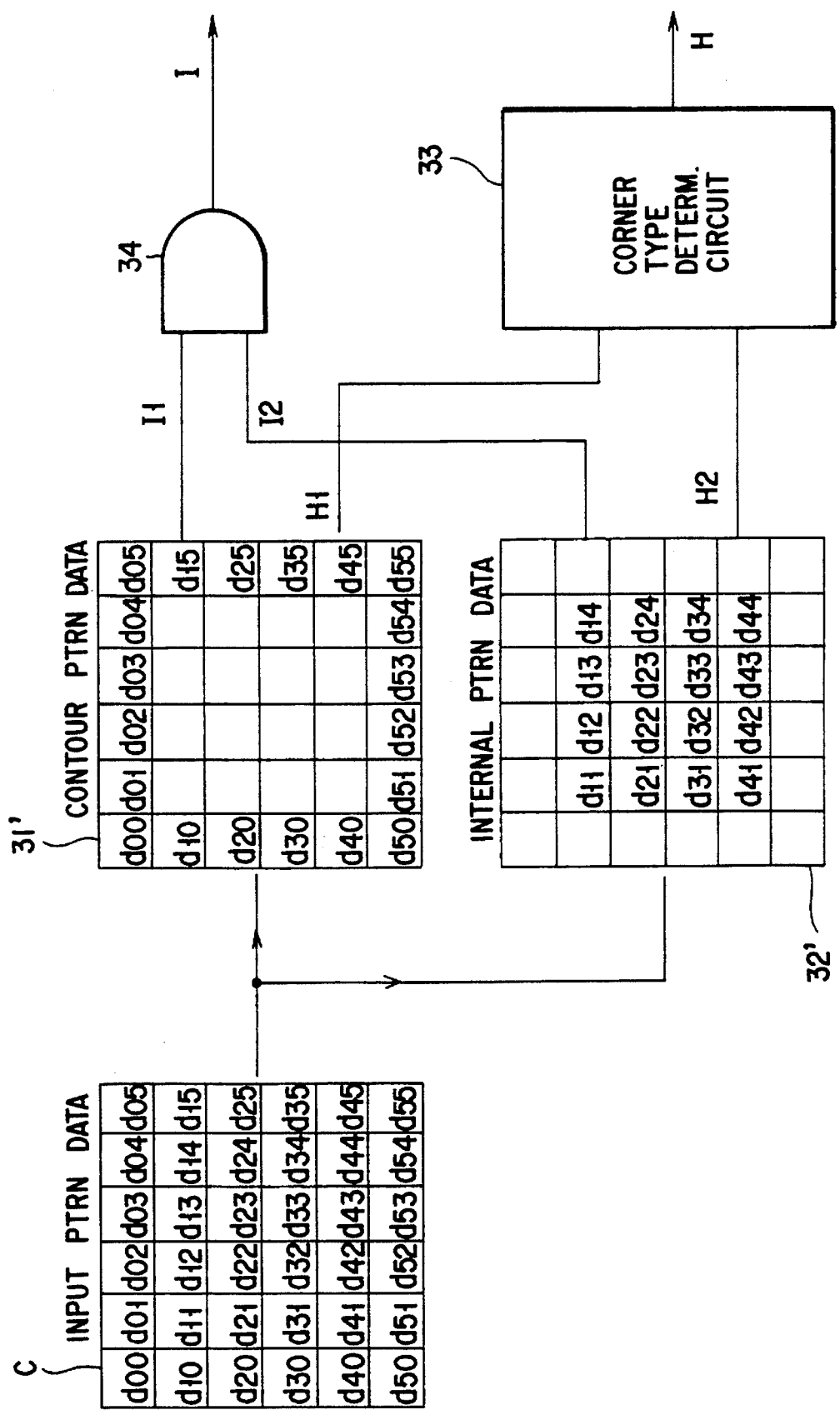
FIG. 6 is a view showing the relationship between an input pattern, a contour pattern, and an internal pattern, and the flow of determination processing for each pattern.

The above-mentioned 6×6 (bit) window is divided into a 20-bit contour portion and a 16-bit internal portion, and these portions are independently tested so that preliminary detection can be performed by using only the 20-bit counter portion to detect whether the bit pattern corresponds to a corner. More specifically, as shown in FIG. 6, a detection window 31' used only for a contour portion and a detection window 32' used only for an internal portion are prepared, and contour pattern data and internal pattern data are independently processed. As a result, a feature coincidence flag I1 associated with contour determination and a feature coincidence flag I2 associated with internal portion determination are generated. This feature detection can be realized by using, e.g., a ROM (Read Only Memory). An input bit pattern is assigned to the address input lines of the ROM in units of bits, and information of coincidence is written in advance at an address of the ROM which corresponds to a predetermined bit combination. For example, a data bit D0 of the ROM is exclusively used in such a manner that "1" is stored in the bit D0 when a feature coincidence is detected, and "0" is stored when noncoincidence is detected.

Furthermore, in order to perform graphic identification by detecting a feature coincidence according to the above-described ROM table scheme, individual ID codes may be output in units of features of detected corners by using the remaining data bits of the ROM, e.g., bits D1 to D3. The types of features are: a feature indicating whether a convex corner is a black or white portion, and a feature indicating the rotational direction of a corner.

Referring to FIG. 6, the detection window 31' used only for a contour portion and the detection window 32' used for an internal portion respectively have the feature determining circuit 31 and 32 of the ROM table scheme described above. The D0 output for the contour feature coincidence flag I1 is also used as an enable signal for the internal portion detection ROM. If peripheral portion determination is "false", internal portion determination is not performed. The corner type determining circuit 33 performs a logical operation of feature extraction data H1 and H2 from two ROMs (i.e., the determining circuits 31 and 32), thus outputting a graphic ID code H.

Hierarchical testing of contour bits will be described next. The 20-bit contour portion of the above-mentioned 6×6 (bit) window is divided into a 4-bit vertex portion and a 16-bit side portion. Of the detection window 31' used only for a contour portion shown in FIG. 6, only vertex bits d00, d50, d05, and d55 are used to perform approximate determination.

Figure 7A:
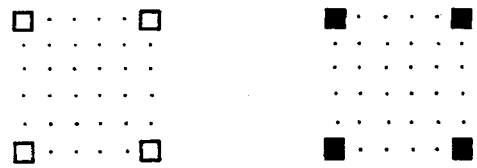
FIGS. 7a, 7b, and 7c are views for explaining bit determination processing at four vertexes (i.e. four corners)
Figure 7B:
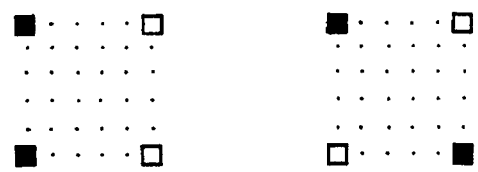
Figure 7C:
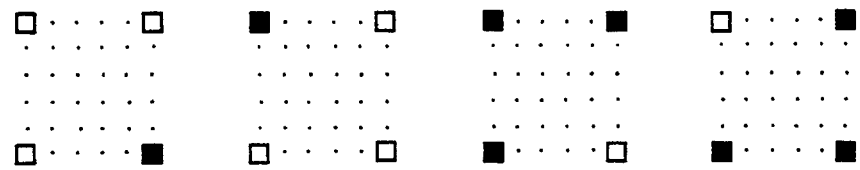

More specifically, processing is performed for each of the cases shown in FIGS. 7a to 7c. The details of the processing will be described below. Note that "!" indicates a not operation (NOT), and "★" indicates a logical product (AND). Referring to FIGS. 7a to 7c, assume that "0", "1", and a bit which is not a target bit are respectively represented by "□", "■", and ".". As shown in FIG. 7a, if all the bits of the four vertexes are "1" or "0", a corner in the window is not a corner to be processed. This operation is represented by the following equation:

non-detection=(d00★d05★d50★d55) or
(!d00★!d05★!d50★!d55)

In addition, as shown in FIG. 7b, if 2 bits of the 4 bits at the vertexes are "0", and the remaining 2 bits are "1", the portion is not a corner to be processed. The portion is not a corner to be processed regardless of whether these 2 bits are located parallel positions or diagonal positions. That is, similar to the above case, $$\begin{aligned}\text{non-detection} = &\ (d00 * !d05 * d50 * !d55)\\ &\text{or } (!d00 * d05 * !d50 * d55)\\ &\text{or } (d00 * d05 * !d50 * !d55)\\ &\text{or } (!d00 * !d05 * d50 * d55)\\ &\text{or } (!d00 * d05 * d50 * !d55)\\ &\text{or } (d00 * !d05 * !d50 * d55)\end{aligned}$$

If 3 bits are "0", and the remaining 1 bit is "1", or 3 bits are "1" and the remaining 1 bit is "0", as shown in FIG. 7c, there is a possibility that the portion corresponds to a corner. An operation coinciding with these conditions is called primary detection. Bits obtained by such primary detection may be examined in more detail.

$$\begin{aligned}\text{primary detection} = &\ (!d00 * !d05 * !d50 * d55)\\ &\text{or } (d00 * d05 * d50 * !d55)\\ &\text{or } (!d00 * !d05 * d50 * !d55)\\ &\text{or } (d00 * d05 * !d50 * d55)\\ &\text{or } (d00 * d05 * !d50 * d55)\\ &\text{or } (d00 * !d05 * d50 * d55)\\ &\text{or } (d00 * !d05 * !d50 * !d55)\\ &\text{or } (!d00 * d05 * d50 * d55)\end{aligned}$$

That is, it can be determined upon determining the vertex bits of the windows that the portions shown in FIGS. 7a and 7b are not corners to be processed. FIGS. 7a to 7c show typical examples. In practice, however, similar processing is performed with respect to windows rotated through 90° with respect to the windows shown in FIGS. 7a to 7c. Since primary selection is completed with this operation, bits corresponding to sides between the vertexes shown in FIG. 7c which change between "0" and "1" may be examined. More specifically, of the side bits indicated by symbols "○" and "●" in FIGS. 8a and 8b, 36 bits between the vertexes which change in the above-described manner are examined. The following determination can be performed on the basis of the relationship between these bits and the bits at the vertexes.

As shown in FIG. 8a, if bits Q in the intervals between the vertex bits which change in the above-described manner, i.e., 4 bits at each of two sides, assume the same value, and all the bits of the included angle assume the same value, it is equivalent to detection of a corner having a predetermined bit configuration. Even if the same determination as in FIG. 7c is achieved, "corner detection" may not be determined depending on the state of the bits Q in the intervals between vertexes which change in the above-described manner, as shown in FIG. 8b.

With this processing, secondary selection is performed. FIG. 5 shows a case wherein the determination result of this secondary selection is output as the contour feature coincidence flag I1. If it is determined in secondary selection that a given portion is not a corner to be subjected to rounding processing, the reference pattern data C is directly output to the distribution function calculator 13 without performing rounding processing.

If it is determined in the above-described secondary selection that the given portion is a corner to be subjected to rounding processing, 16 bits of the internal portion detection window 32' are tested to determine whether the portion is really a corner to be subjected to rounding processing. If it is determined that the portion is a corner to be subjected to rounding processing, the masking pattern data J corresponding to the corner pattern to be rounded is generated by the masking pattern data generator 22. The reference pattern data C is performed rounding processing of a corner portion on the basis of the data J. With this rounding processing, a rectangular graphic pattern as shown in FIG. 3a is changed into a curved graphic pattern as shown in FIG. 4. Thereafter, the data D which has undergone this rounding processing is output to the distribution function calculator 13.

As described above, according to the first embodiment, since corner rounding processing is performed with respect to the reference pattern data C bit-developed by the bit pattern generating circuit 11 by the corner rounding circuit 12 constituted by the corner pattern detection window circuit 21, the masking pattern data generator 22, and the graphic pattern synthesizer 23, a reference pattern can be approximated to an actual target pattern having rounded corners. Therefore, the threshold value range for comparing/testing errors can be narrowed as compared with the one set in the conventional inspection apparatus, thus allowing detection of a defect which exists near a corner and cannot be detected by the conventional apparatus. That is, a defect near a corner can be reliably detected without causing any false-defect in a pattern. Consequently, the pattern testing precision can be greatly improved.

Furthermore, according to the first embodiment, in the corner pattern detection window circuit 21, the contour pattern of a corner pattern detection window and the internal pattern excluding the contour portion are independently tested, and testing/determination of corner pattern coincidence is performed by the logical operation between the test result of the contour pattern and the test result of the internal pattern, thereby simplifying the processing required for corner pattern detection and shortening the time required therefor. If a target pattern does not coincide with a corner pattern, determination of removal can be made before logical search proceeds too far. Consequently, the throughput is increased.

(Second Embodiment)

The second embodiment of the present invention will be described next. Several patterns can be considered as corner rounding shapes, as shown in FIGS. 10a to 10c. The optimal pattern varies depending on the state of an actual target mask, and it is illogical to fix one pattern for an apparatus. Therefore, as shown in FIG. 9, in the second embodiment, a plurality of (e.g., three) masking pattern data generators 22 are arranged to prepare several rounded patterns as tables for one corner. In addition, a corner rounding shape selector 29 is arranged to switch the rounded patterns by means of a table selection scheme.

In performing determination processing to select an optimal table, a state which can realize the minimum pseudo-defect rate in testing a mask is selected in accordance with an external rounding shape command. As a modification (not shown) of this embodiment, an apparatus may be designed to fetch an evaluation function corresponding to the minimum pseudo-defect rate so as to perform self-sustaining control of selection of rounded pattern tables.

In order to form a table which can be externally updated, a semiconductor memory can be used as hardware. A case in which a RAM (Random Access Memory) is used will be described. If a RAM is used, both a corner pattern detecting function and a masking pattern data generating function can be realized at the same time. That is, a bit pattern is input to an address line, and an output is obtained from a data line. A masking pattern or a feature coincidence flag corresponding to a processing result may be written at an address corresponding to a target bit combination.

The required capacity of the RAM is determined by the number of bits for detecting a corner pattern. More specifically, if a pattern is to be detected by using 6×6 bits for the 4-bit corner rounding processing, the RAM has a 20-bit address area for detection of peripheral bits, and has a capacity corresponding to the number of bits required for corner type information and a feature coincidence flag. In addition, the RAM requires not only a 16-bit address area for processing an internal portion of 4×4 bits, and a capacity corresponding to the number of bits required for corner type information and a feature coincidence flag, but also a capacity for outputting 16-bit data to generate a 4×4 (bit) masking pattern. In this case, corner type information includes information indicating the direction in which a corner exists, information indicating whether a corner is a white or black corner, and the like.

In a normal operation, such a RAM serves as a look-up table in the circuit. If, however, the RAM is designed to be operated/updated through a host control circuit/unit, determination processing can be flexibly performed.

The present invention is not limited to the first and second embodiments described above. In the above embodiments, one side of a bit pattern is constituted by 6 bits. However, the above-described scheme of detecting a corner by using both vertex bits and side bits can be effectively applied to pattern data having a larger bit configuration. In the above embodiments, the number of bits by which a corner is cut off (expanded) is expressed by the number of bits of corner sides, and a 6×6 (bit) window is used for 4-bit rounding processing. However, n-bit processing (n=1 or more) can be realized by preparing a window having an (n+2)-bit matrix configuration. In addition, if it can be determined by only testing a contour pattern whether a target pattern is a corner portion to be subjected to rounding processing, testing of an internal pattern can be omitted. Although the graphic pattern synthesizer performs exclusive OR processing, any logical processing can be employed as long as a corner portion can be rounded by synthesizing reference pattern data with masking pattern data. If reference pattern data sufficiently close to test pattern data can be obtained by using only the corner rounding circuit 12, extraction of a corner by the feature extracting circuit 14 may be omitted. Furthermore, if a threshold value for comparison is not changed depending on the feature of an entirely black or white pattern other than a corner pattern, an edge portion of a pattern, or the like, the feature extracting circuit 14 itself can be omitted.

In the first and second embodiments, the pattern inspection apparatuses are based on corner rounding processing. However, the present invention is not limited to an apparatus based on corner rounding processing but can be applied to an apparatus designed to detect a corner portion and compare/collate reference pattern data with test pattern data. That is, if an actually formed pattern has a small number of rounded portions, the corner (pattern) detection window circuit 21 shown in FIG. 5 may be used as a feature extracting circuit, and the threshold value level of the comparing/determining circuit may be changed in accordance with an output from the circuit 21. In this case, although the effect of rounding processing cannot be obtained, the processing required for feature extraction (detection of a corner portion) can be simplified, and the time required therefor can be shortened as compared with the conventional apparatus.

As described in detail above, according to the present invention, the occurrence of pseudo-defects caused by rounded corners can be prevented by comparing reference pattern data, obtained from design pattern data, with test pattern data upon performing rounding processing of the reference pattern data. In addition, defects which are present near corners can be reliably detected. As a result, the pattern precision can be improved.

(Third Embodiment)

Figure 11:
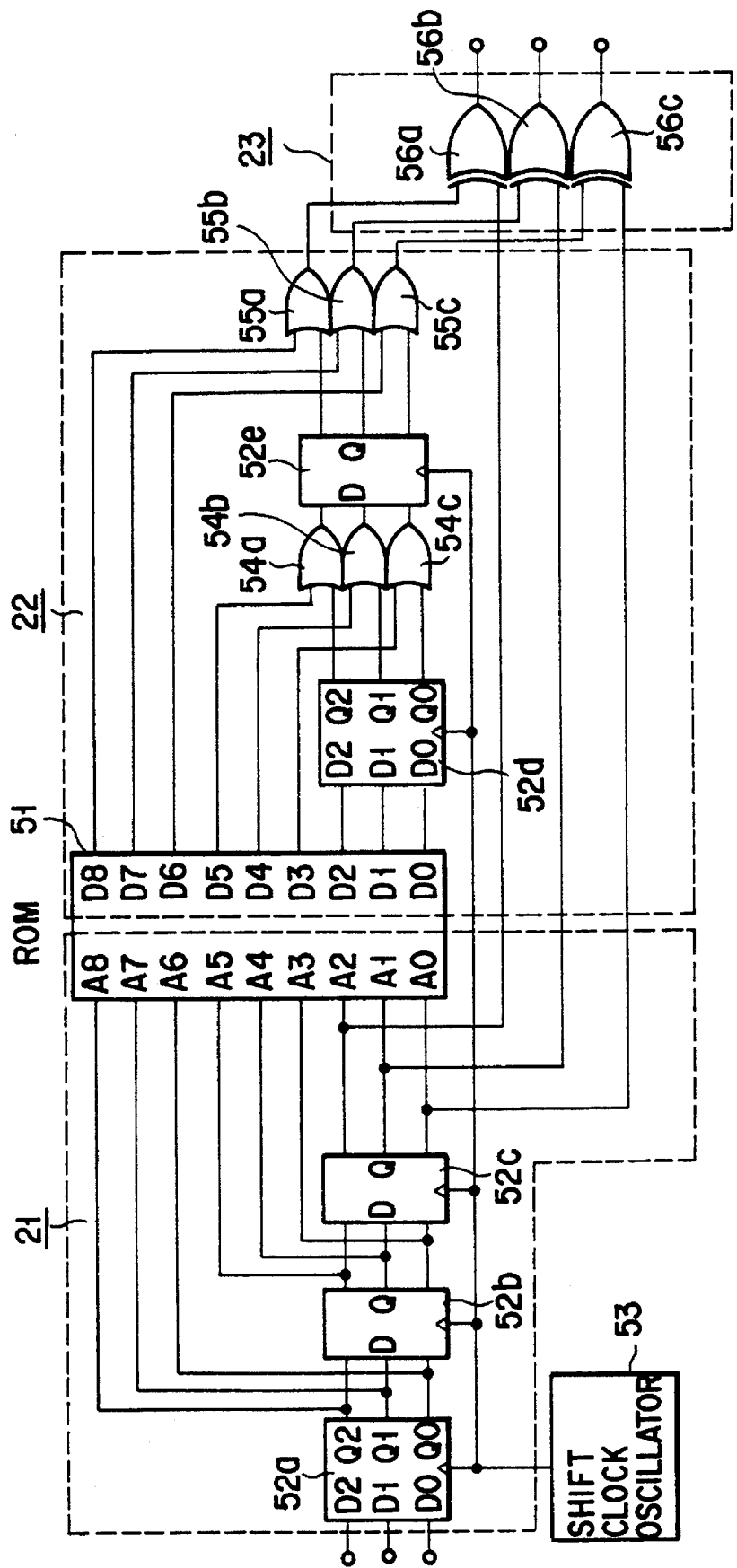
FIG. 11 is a circuit diagram showing the corner rounding circuit in FIG. 2 in more detail.
Figure 12A:
FIGS. 12a to 12d are views showing corner pattern detection templates of different numbers of bits.
Figure 12B:
Figure 12C:
Figure 12D:
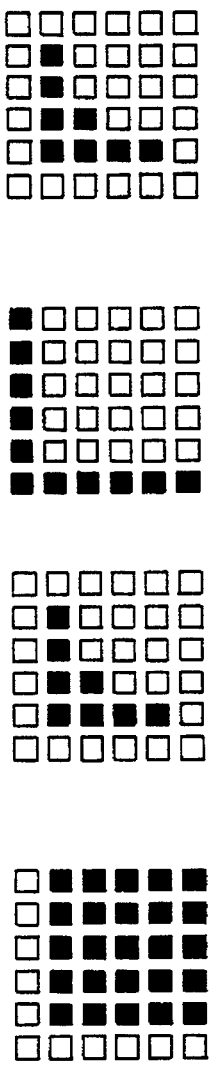

FIG. 11 shows a detailed arrangement for performing 1-bit rounding processing. Referring to FIG. 11, reference numeral 51 denotes a ROM; 52 (52a to 52e), latches; 53, a shift clock oscillator; 54 (54a to 54c) and 55 (55a to 55c), OR gates; and 56 (56a to 56c), EX-OR (exclusive-OR) gates. The actual constituent elements are arranged as follows. As indicated by the connection relationship in FIG. 11, a corner pattern detection window circuit 21 is constituted by the ROM 51 and the latches 52a to 52c. A masking pattern data generator 22 is constituted by the ROM 51, the latches 52d and 52e, and the OR gates 54 and 55. In addition, a graphic pattern synthesizer 23 is constituted by the EX-OR gates 56.

The corner pattern detection window circuit 21 has a function of detecting two-dimensional pattern matching and can be constituted by various means. Assume, in this case, the circuit 21 constituted by a ROM. If a ROM is used, both a corner pattern detecting function and a masking pattern data generating function can be realized at the same time. The required capacity of the ROM is determined by the number of bits used for corner pattern detection.

If a pattern is to be detected by using 3×3 bits, a ROM having address lines corresponding to 9 bits and a 9-bit data output is required. If a 4×4 (bit) window is to be formed, a ROM having address lines corresponding to 16 bits and a 16-bit data output is required. If the number of bits by which a corner is cut off (or expanded) is expressed by the number of bits at corner sides, a corner pattern detection window of this embodiment requires a (n+2)-bit matrix in n-bit rounding processing.

FIGS. 12a to 12d respectively show the states of corner pattern detection corresponding to 1- to 4-bit rounding processing. In the embodiment shown in FIG. 11, a ROM having an input/output of 3×3=9 bits is used for 1-bit rounding processing.

Figure 13:
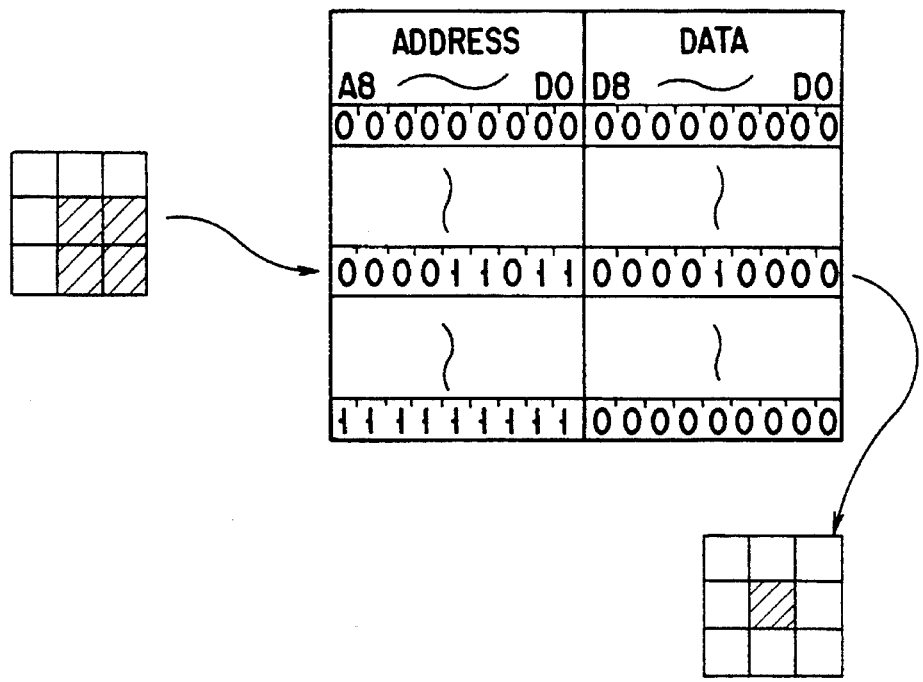
FIG. 13 is a view showing the state of data to be written in a ROM used in the arrangement shown in FIG. 11.

FIG. 13 shows a state wherein data to be written in the ROM used in the arrangement shown in FIG. 11 is converted. White and black pattern portions of an original graphic pattern are respectively represented by "0" and "1". When a pattern to be scanned/detected is supplied to the address lines of the ROM, an address in the ROM is uniquely determined in accordance with the input pattern. If the input pattern has a predetermined bit configuration, masking pattern data corresponding to the graphic pattern are written at the address in advance. If the input pattern does not correspond to a pattern to be subjected corner rounding processing, all the bits of masking pattern data to be written are "0".

Referring to FIG. 11, strip data of an original graphic pattern is shifted and latched by the data latch 52a in accordance with a clock generated by the shift clock oscillator 53. Latch results from the latches 52a to 52c are supplied to the address lines of the ROM 51, and a two-dimensional pattern of 3×3 bits can be tested.

Figure 14A:
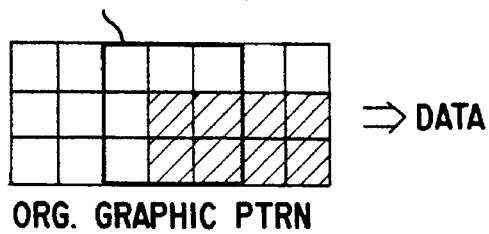
FIGS. 14a to 14c are views showing the scanning direction in bit shift processing.
Figure 14B:
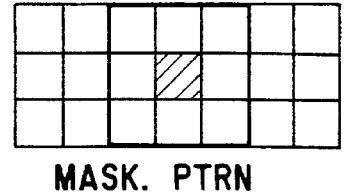
Figure 14C:
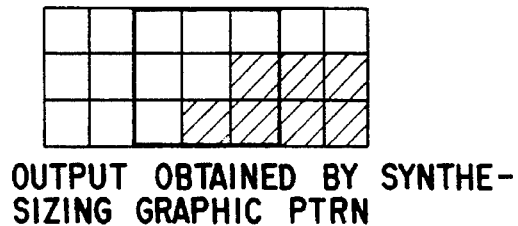

As shown in FIGS. 14a to 14c, in the ROM 51, a 3×3 (bit) pattern is scanned while it is shifted bit by bit. Subsequently, 3×3 (bit) masking data as a detection result is obtained at once. However, in order to match the timings of the masking data and the original graphic pattern in pipeline processing, the masking data is temporarily held in the delay latches 52d and 52e in units of three bits, and the data is input to the EX-OR gates 56a to 56c which have the function of a graphic pattern synthesizer.

A mask pattern corresponding to the bits input to terminals A0 to A2 of the ROM 51 is output from terminals D6 to D8 and is directly input to the EX-OR gates 56 serving as the graphic pattern synthesizer 23 within a clock period. A mask pattern corresponding to the bits input to terminals A3 to A5 is output from terminals D3 to D5 and is delayed by the delay latch 52e by an amount corresponding to one clock. The resultant data is input to the EX-OR gates 56. A mask pattern corresponding to the bits input to terminals A6 to A8 is output from terminals D0 to D2 is delayed by the delay latches 52d and 52e by an amount corresponding to two clocks. The resultant data is input to the EX-OR gates 56. The OR gates 54 and 55 are required to perform corner rounding processing of independently detected adjacent corner during a scanning operation of the corner detection window circuit 21.

In the third embodiment, corner pattern detection of a 3×3 (bit) pattern is performed, and 1-bit rounding processing is performed. If a large number of bits are to be processed, a ROM requires address and data lines corresponding to a predetermined bit count. In addition, the width of data simultaneously latched by delay latches is increased, and a predetermined number of delay stages is required.

As described above, according to the third embodiment, since corner rounding processing is performed with respect to reference pattern data C bit-developed by a bit pattern generating circuit 11 by a corner rounding circuit 12 constituted by the corner pattern detection window circuit 21, the masking pattern data generator 22, and the graphic pattern synthesizer 23, a reference pattern can be approximated to an actual target pattern having rounded corners. Therefore, the threshold value range for comparing/testing errors can be narrowed as compared with the one set in the conventional testing apparatus, thus allowing detection of a defect which is present near a corner and cannot be detected by the conventional apparatus. That is, a defect near a corner can be reliably detected without causing any false-defect. Consequently, the pattern inspecting precision can be greatly improved.

(Fourth Embodiment)

In general, the degree of corner rounding varies depending on the conditions of development and a resist in the manufacturing process of a mask. Therefore, in the fourth embodiment shown in FIG. 15, the maximum number of bits to be subjected to corner rounding processing can be changed in accordance with a signal L from an external circuit. For this purpose, in a corner pattern detection window circuit 21, all the corner pattern detecting operations of 1 to 4 bits shown in FIGS. 12a to 12d are always performed, and a pattern having a larger number of bits to be rounded is preferentially transmitted to a masking pattern generator 22. The maximum number of bits to be rounded is defined by external setting, and a corner pattern of the maximum pattern configuration is detected with an externally set bit count (L) or less. External setting by this signal L can be independently performed with respect to convex and concave corners, and can be independently performed with respect to white and black patterns.

The position of a corner pattern to be subjected to corner rounding processing in stripe data is indefinite. For this reason, as shown in FIG. 16, a corner pattern detection window circuit 21 is designed such that corner pattern detection window circuits are stacked on each other while they are shifted from each other in the direction of width of stripe data by one bit, thus covering the entire range of the stripe width.

Figure 16:
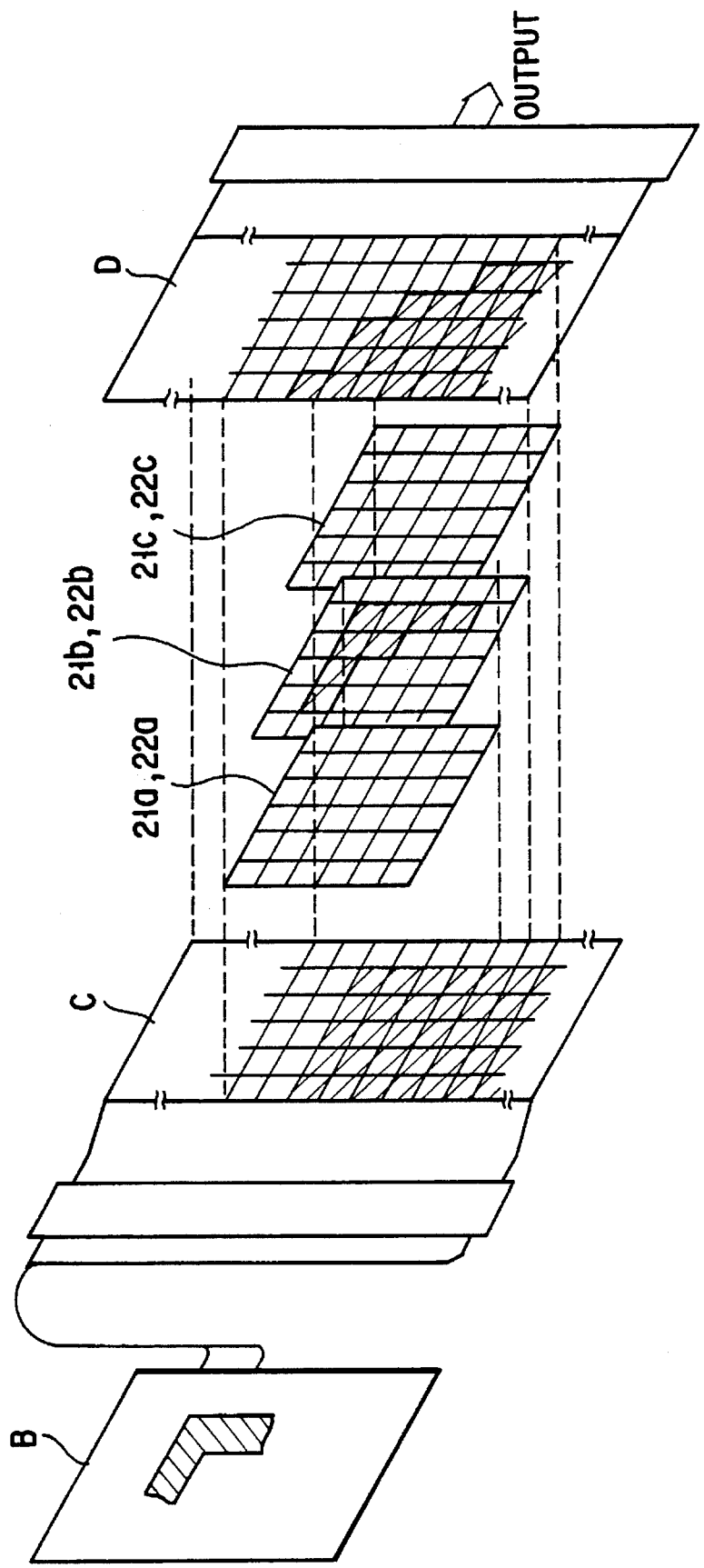
FIG. 16 is a view showing the relationship between a corner pattern and a masking pattern.

Corner pattern detection window circuits 21a to 21c and masking pattern generators 22a to 22c in FIG. 16 respectively correspond to the corner patterns and the masking patterns in FIG. 3a. In the previous embodiment, assuming that adjacent corners are present in the data width direction, similar to the processing with respect to the adjacent bits in the scanning direction shown in FIGS. 14a to 14c, generated masking pattern data are ORed and synthesized while they are shifted bit by bit in the widthwise direction. In the case shown in FIG. 16, since patterns detected by the corner pattern detection window circuits 21a and 21c do not coincide with corners to be detected, the masking pattern data generators 22a and 22c generate data "0".

Since a pattern detected by the corner pattern detection window circuit 21b coincides with a corner to be detected, the masking pattern data generator 22b generates predetermined masking pattern data. The masking pattern data generator 22 shifts the masking patterns generated by the generators 22a to 22c from each other by 1 bit, and synthesizes the data with each other by performing OR processing in units of bits. In addition, the data generated by the generator 22b is directly output as the synthesized masking pattern data. Consequently, the corner rounding result after the graphic pattern synthesizing operation can be obtained.

The corner pattern detection window circuits 21a to 21c require not only bits to be subjected to rounding processing but also peripheral bit pattern data extending from the target bits in all the directions by 2 bits. In addition, if the corner pattern detection window circuits are stacked on each other while they are shifted from each other in the direction of width of stripe data by 1 bit, as shown in FIG. 16, the following phenomena occur at the boundaries of stripe widths. In the conventional apparatus, if the stripe data C shown in FIGS. 35a to 35c is input to the corner pattern detection window circuit 21, the following problems are caused: (1) some corners at this portion cannot be detected; (2) if a corner is detected, rounding processing extends to a bit pattern included in the previous stripe data but it cannot be performed; and (3) similarly, rounding processing extends to a bit pattern included in the next stripe data, but it cannot be performed.

(Fifth Embodiment)

In the fifth embodiment shown in FIG. 17, therefore, stripe data C is input to a corner pattern detection window circuit 21, and a portion of the stripe data C which has a predetermined width and is in contact with a succeeding stripe is stored in a stripe data buffer 24. The part of the previous stripe data which is stored in the buffer 24 is added to the succeeding stripe data. The resultant data is input to the corner pattern detection window circuit 21. The corner pattern detection window circuit 21 performs corner detection throughout a range of a predetermined stripe data width or more. Inaccurate detected portions in the data width direction are removed, and only portions obtained by proper corner pattern detection are output to a masking pattern data generator 22. In this case, the data width required for the stripe data buffer 24 and the extra number of bits which are to be observed by the corner pattern detection window 21 are determined by the maximum number of bits to be subjected to corner rounding processing.

The present invention is not limited to the above-described embodiments. Various changes and modifications can be made within the scope and spirit of the invention. For example, in the previous embodiment, the graphic pattern synthesizer performs exclusive OR processing. However, any logical processing can be employed as long as a corner portion can be rounded by synthesizing reference pattern data with masking pattern data. If reference pattern data sufficiently close to test pattern data can be obtained by using only the corner rounding circuit, extraction of a corner by the feature extracting circuit may be omitted. Furthermore, if a threshold value for comparison is not changed depending on the feature of an entirely white or black pattern, an edge portion of a pattern, or the like, the feature extracting circuit itself can be omitted.

(Sixth Embodiment)

Figure 18:
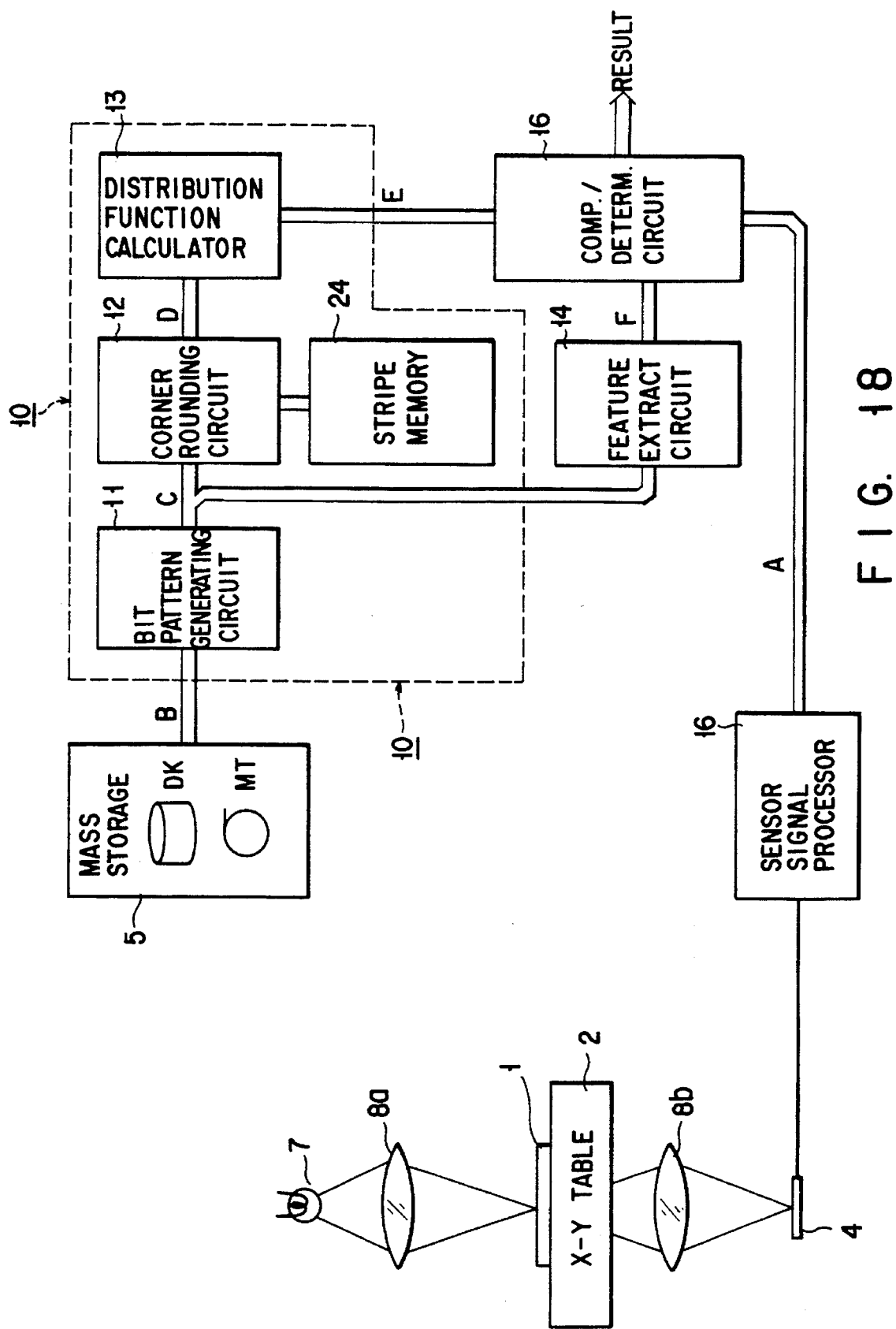
FIG. 18 is a block diagram showing a schematic arrangement of a pattern inspection apparatus according to the sixth to eighth embodiments of the present invention.

FIG. 18 is a block diagram showing a schematic arrangement of a pattern testing apparatus according to the sixth to eighth embodiments of the present invention. A pattern on a reticle 1 to be tested, which is placed on an X-Y table 2, is radiated by an illumination light source 7 and an illumination optical system 8a and is projected on a one-dimensional sensor array 4 by a testing optical system 8b. An output from the one-dimensional sensor array 4 is converted into observation data (test pattern data) as a digital signal by a sensor signal processor 16. The data is then supplied to a comparing/determining circuit 6. Since the one-dimensional sensor 4 is not long enough to scan the target reticle 1 at once, the X-Y table 2 continuously moves at a constant speed in, e.g., the Y direction, thus performing a testing operation in units of stripes. In addition, the entire pattern formation region on the target reticle 1 is scanned by intermittently driving the X-Y table 2 in the X direction perpendicular to the Y direction.

Design pattern data B supplied from a computer 5 is developed into reference pattern data C, expressed by a bit pattern, by a bit pattern generating circuit 11 of a reference signal generator 10. This reference pattern data C is supplied to a corner rounding circuit 12 and a feature extracting circuit 14. The corner rounding circuit 12 performs corner rounding processing (to be described later) on the basis of the reference pattern data C, and outputs a result D to a distribution function calculator 13. An output E from the distribution function calculator 13 is supplied to the comparing/determining circuit 6 to be compared with pattern data A obtained from the test pattern.

In this case, the corner rounding circuit 12 simulates rounding of a corner portion of a pattern in a process after a drawing operation, and approximates rounding of the observation data A by rounding a corner of the reference pattern data C, thereby preventing erroneous determination that a rounded corner portion is a defect. A stripe memory 24 connected to the corner rounding circuit 12 stores data of stripe connecting portions which are required for the corner rounding circuit 12 and the distribution function calculator 13. The distribution function calculator 13 performs weighting/addition and multivalue conversion of the design data by using a point spread function representing the resolution of the testing optical system 8b, thus forming final reference data. Strictly speaking, the corner rounding circuit 12 and the distribution function calculator 13 operate sequentially on reference pattern data C approximate rounding of observation data.

The feature extracting circuit 14 extracts a feature indicating whether a graphic pattern in a region which is being tested is a corner or a portion other than a corner, i.e., an entirely black pattern, an entirely white pattern, or an edge portion of a pattern, and changes a threshold value F, used for error determination in a comparing/testing operation, for each feature. The comparing/determining circuit 6 compares/collates the reference pattern data E with the observation data A to detect their difference. If this difference exceeds the threshold value F of the graphic pattern in the region which is being tested, the presence of a defect is determined.

Figure 19:
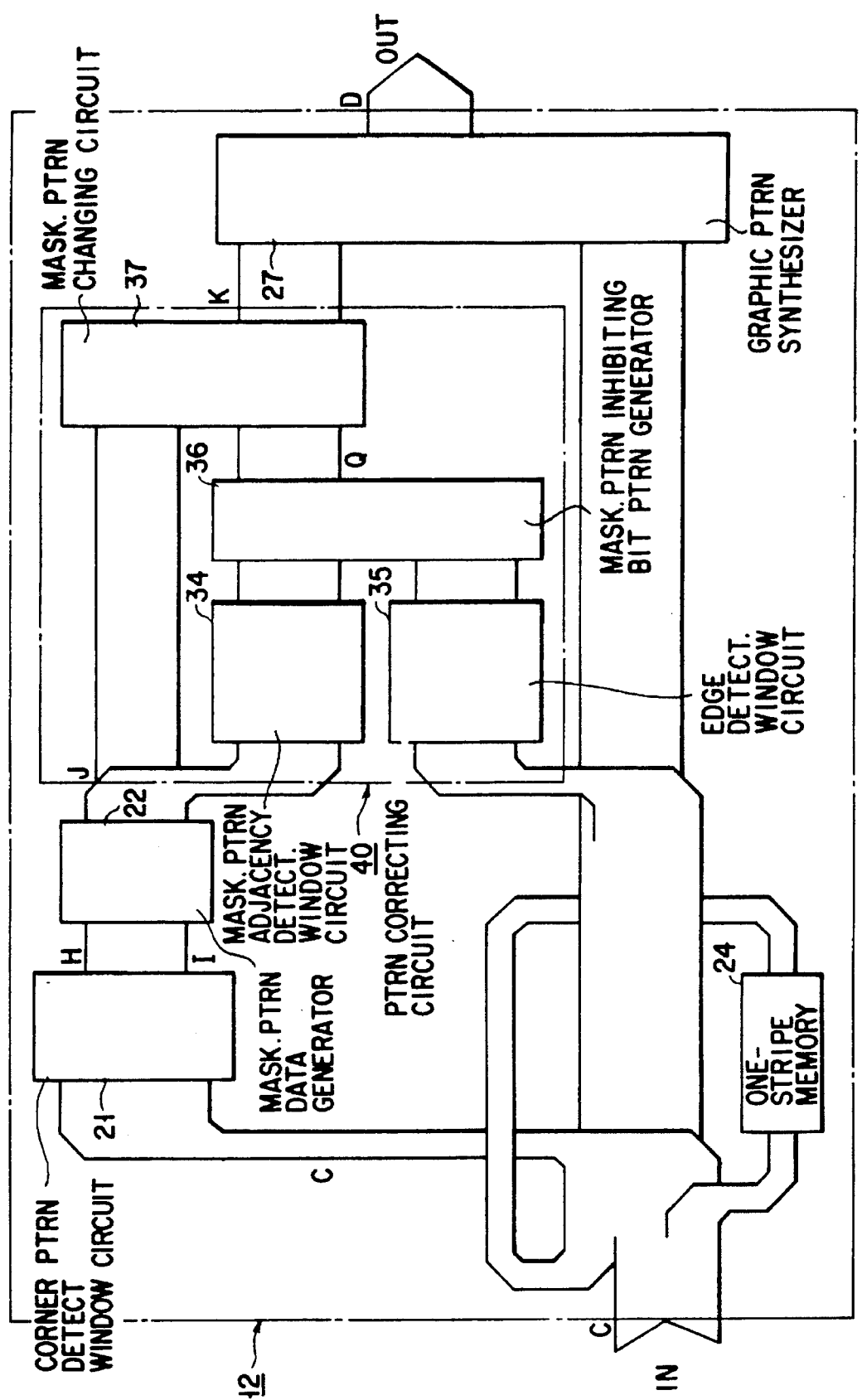
FIG. 19 is a block diagram showing a schematic arrangement of a corner rounding circuit used in the sixth embodiment.

In the sixth embodiment shown in FIG. 19, the corner rounding circuit 12 is constituted by a corner pattern detection window circuit 21, a masking pattern data generator 22, a masking pattern changing circuit 37, a masking pattern adjacency detection window circuit 34, an edge detection window circuit 35, a masking pattern inhibiting bit pattern generator 36, and a graphic pattern synthesizer 27. A corner-rounded pattern correcting circuit 40 is constituted by the elements respectively denoted by reference numerals 34 to 37 (to be described in detail later).

Each of the components constituting the corner rounding circuit 12 will be described. (A portion excluding the corner-rounded pattern correcting circuit 40 will be described first.)

Every time the reference pattern data C as stripe data is input, the corner pattern detection window circuit 21 detects, by using a corner pattern detection template, whether a pattern to be subjected to corner rounding processing is included. If, for example, the corner pattern detection window circuit 21 detects a pattern to be subjected to corner rounding processing, the circuit 21 sets a graphic pattern code representing the detected graphic pattern and turns on a flag I (ON) representing that the pattern coincides with the feature.

The masking pattern data generator 22 outputs masking pattern data J corresponding to the graphic pattern code H output from the above-described corner pattern detection window circuit 21. This masking pattern data J is designed such that data "1" are set in the original graphic pattern prior to corner rounding processing at the positions of bits to be subjected to black and white inversion, and data "0" are set at other positions. FIGS. 3a and 3b respectively show the corner patterns detected by the corner pattern detection window circuit 21 and the masking patterns corresponding to the original graphic patterns generated by the masking pattern data generator 22. A masking pattern K is input to the graphic pattern synthesizer 27. The graphic pattern synthesizer 27 performs an exclusive-OR (EX-OR) operation in units of bits on the basis of a corner pattern (original graphic pattern) C and the masking pattern K. That is, in the original graphic pattern C, only the bits corresponding to the "1"-level bits of the masking pattern K are subjected to black and white monochrome inversion (i.e., exchange of data "1" and data "0"). For example, if the original graphic pattern is a convex corner pattern, this operation is equivalent to an operation of cutting off the corner. If it is a concave corner pattern, the corner is expanded. An output from the graphic pattern synthesizer 27, which is obtained by the above-described series of corner rounding operations, is the rounded graphic pattern shown in FIG. 4 based on the corner pattern (the original pattern shown in FIGS. 3a and 3b).

In the case shown in FIGS. 3a and 3b, a 6×6 (bit) window for 4-bit rounding processing is exemplified. The number of bits to be rounded is not limited to 4. For example, corner pattern detection may be performed in accordance with 1- to 4-bit rounding processing shown in FIGS. 12a to 12d.

Figure 20:
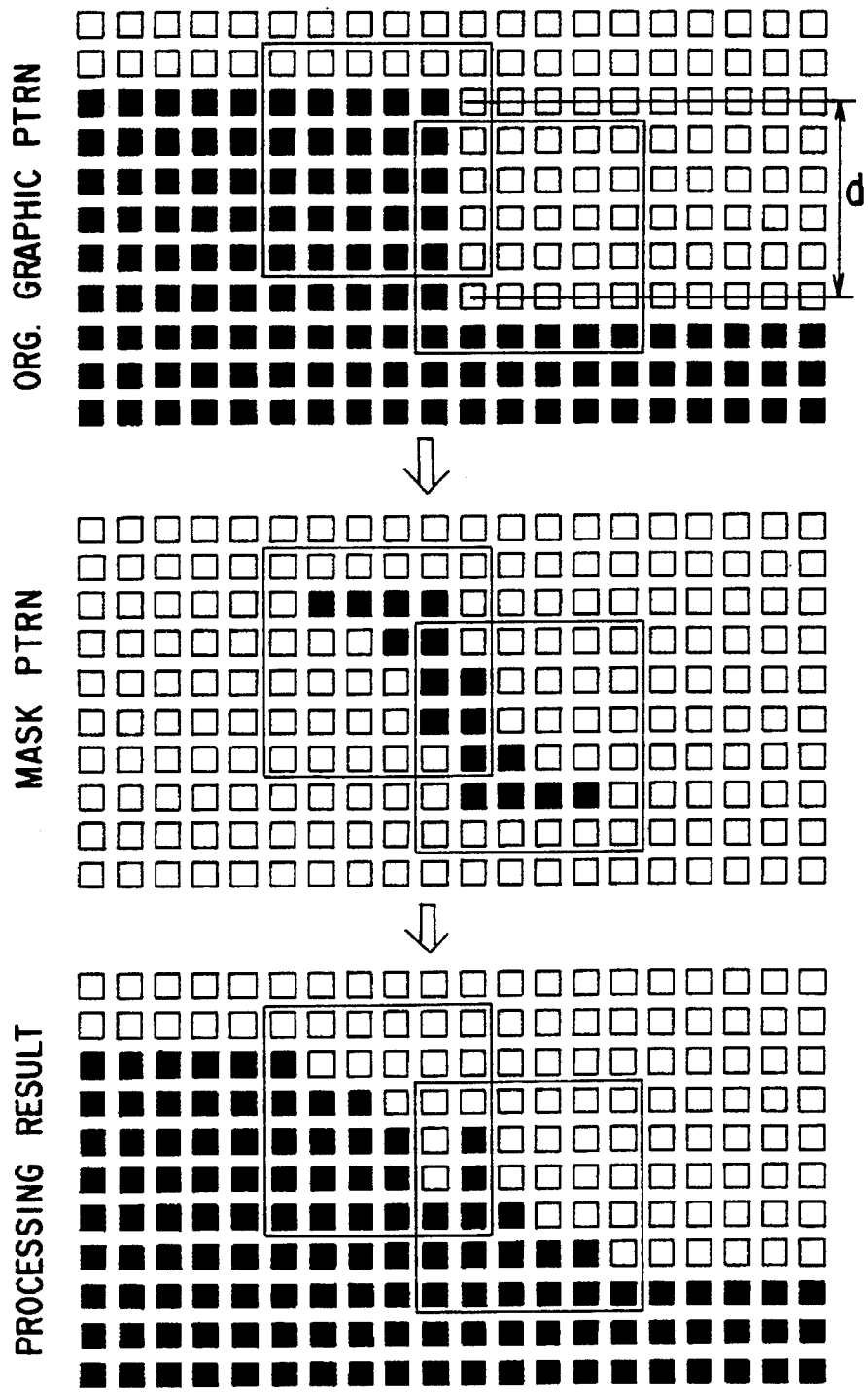
FIG. 20 is a view showing a result of corner rounding processing in a case wherein the distance between corners to be rounded is close.
Figure 22A:
FIGS. 22a to 22d are views respectively showing typical examples of rounding processing performed by the corner rounding circuit.
Figure 22B:
Figure 22C:
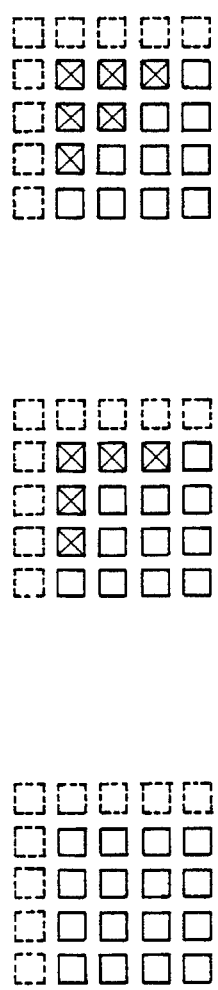
Figure 22D:
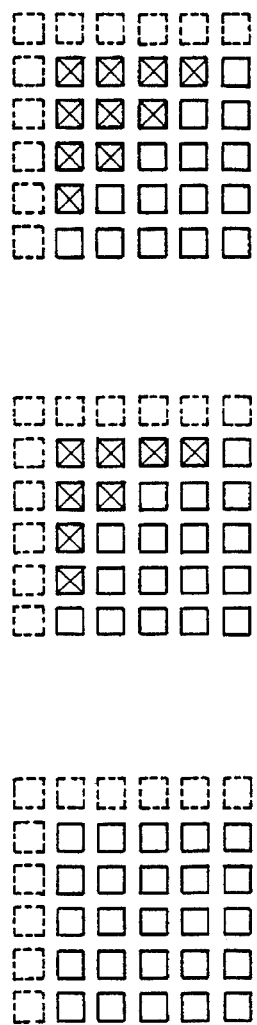
Figure 27:
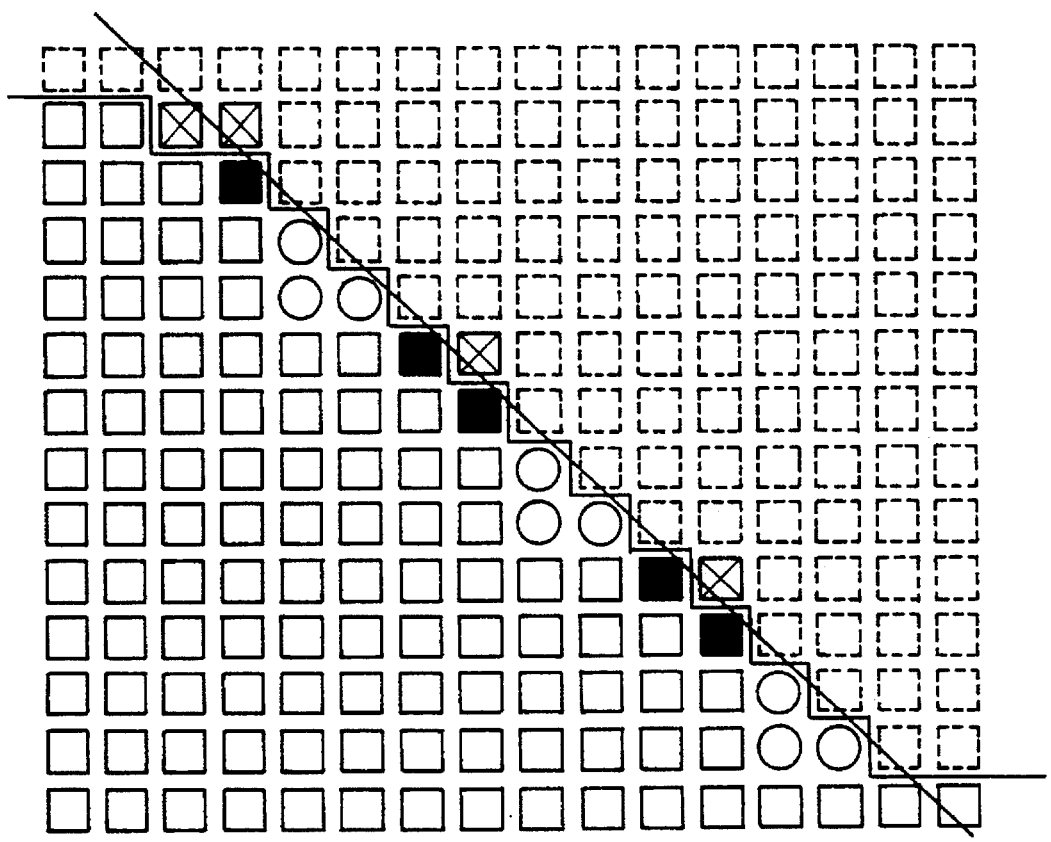
FIG. 27 is a view showing a pattern obtained by correcting the pattern shown in FIG. 24.

Note that a distance d between the respective corners of a corner pattern (original graphic pattern in FIG. 3) is larger than the size of a masking pattern used for rounding processing. If, however, the distance d between the respective corners of a corner pattern is smaller than the size of a mask pattern used for rounding processing, as in the case wherein a mask pattern closer to those shown at the lower positions in FIGS. 3a and 3b is used for the corner pattern shown in FIG. 20, an unexpected result (i.e. excessive rounding pattern) which cannot be obtained in an actual reticle manufacturing process is obtained, as shown in FIG. 20. This phenomenon occurs because the corner rounding circuit 12 independently recognizes the respective corners, and generates adjacent masking patterns shown in the mask pattern in FIG. 20.

If the above-described pattern is generated, reference data which does not correspond to an actual pattern is input to the comparing/determining circuit 17. As a result, it is determined that a defect is detected, in spite of the fact that there is no actual defect. In order to solve this problem, the corner-rounded pattern correcting circuit 40 is arranged between the circuits 22 and 27.

The following scheme may be considered as one of the schemes for preventing the generation of reference data which is generated when the distance between the respective corners to be rounded is smaller than the size of a mask pattern used for rounding processing but cannot be obtained in an actual reticle manufacturing process. In the scheme, the range of the corner pattern detection window circuit 21 in which an original graphic pattern is referred to is widened to detect a corner in consideration of the adjacency of corners so that the masking pattern data generator 22 outputs a masking pattern in consideration of the adjacency of the corners. In this scheme, however, since the reference range is two-dimensional, even a slight increase in size of the window causes an abrupt increase in the number of pixels to be referred to by the corner pattern detection window circuit 21. Since the size of a circuit for realizing this processing is also greatly increased, the scheme is not practical.

As another scheme, adjacent masking patterns may be detected. However, the range in which masking patterns must be scanned is not significantly different from the widened range of the corner pattern detection window circuit 21 in which an original graphic pattern is referred to. In addition, it is very difficult to recognize that masking patterns are adjacent to each other, because the masking patterns have irregular shapes.

The corner rounding pattern correcting circuit 40 in the sixth embodiment, therefore, detects the adjacency of masking patterns, which is caused when the distance between the respective corners to be rounded is smaller than the size of a masking pattern to be used for rounding processing, by detecting an edge of a preprocessing reference pattern, (original graphic pattern) obtained prior to exclusive OR processing, and the presence of masking patterns on both the sides of the edge on the basis of the pre-processing reference pattern and a masking pattern corresponding to the pre-processing reference pattern, generates a masking pattern inhibiting bit pattern corresponding to the shape of the scanned/detected adjacent masking pattern, and removes masking pattern data of a portion in which the masking pattern inhibiting bit pattern exists, thereby achieving the above object.

The patterns of stripe data detected by the corner pattern detection window circuit 21 of the corner rounding circuit 12, masking patterns output from the masking pattern data generator 22, and portions of the masking patterns which are changed by the corner-rounded pattern correcting circuit 40 will be displayed and described by using the symbols shown in FIG. 21. When one pattern is considered, 16 variations, i.e., four rotational directions ×two types of mirror images× two types of black and white inversion, can be considered. Only one typical type will be shown.

Consider first a case wherein over-corrected patterns are generated. FIGS. 22a to 22d show original graphic patterns detected by the corner rounding circuit 12 and typical examples of rounded patterns. In this case, type A indicates a case wherein the rounded portion of a corner portion is approximated to a circular arc, and type B indicates a case wherein the rounded portion is cut off with a 45° oblique line. In a reticle manufacturing process, since a white protruding portion and a black protruding portion are rounded in different manners, the rounding amounts of the white and black protruding portions must be independently set. The maximum rounding amount may be set as follows. If the rounding amount in a process can be set to be large, since it may mean that the testing precision can be decreased, "3-bit rounding" may be set as the maximum rounding amount. Even in a case wherein some difference is to be set between the rounding amounts of white and black protruding portions, at most "4-bit rounding" for either a white protruding portion or a black protruding portion may be considered.

FIGS. 23a to 23d show examples of over-corrected patterns to be corrected which are generated when the above-described scheme is applied to the stepped stripe data shown in FIG. 20. Referring to FIGS. 23a to 23d, each solid line extending between squares, each corresponding to 1 bit, indicates the boundary between white and black portions after rounding processing. It is apparent from these examples that an over-corrected pattern is generated when masking patterns are set side by side through a vertical white/black boundary. In addition, as shown in FIG. 24, if rounding processing is performed with respect to stripe data in which steps of the same sizes continuously appear, concave portions of an original graphic pattern protrude and convex portions withdraw. That is, so-called phase inversion may occur. It is apparent from these examples that a pattern in which phase inversion occurs is generated when masking patterns are obliquely set side by side through a white/black boundary.

It is clear from the above-described fact that the generation of an excessive rounding pattern can be prevented by detecting and correcting masking patterns which are adjacent to each other through a white/black boundary. When all arrangements of masking patterns by which the excessive round patterns shown in FIGS. 22a to 22d are generated are examined, it is found that the generation of excessive round patterns can be prevented by detecting the masking patterns and the stripe patterns shown in FIGS. 25a to 25f and changing the masking patterns. (i.e. four-graphic elements in left side of each Fig. are corresponding to the center of the twelve-graphic elements in right side of each Fig.) FIGS. 26a to 26d and FIG. 27 show examples of patterns obtained by applying this procedure to the patterns shown in FIGS. 23a to 23d and FIG. 24.

(Seventh Embodiment)

Figure 28:
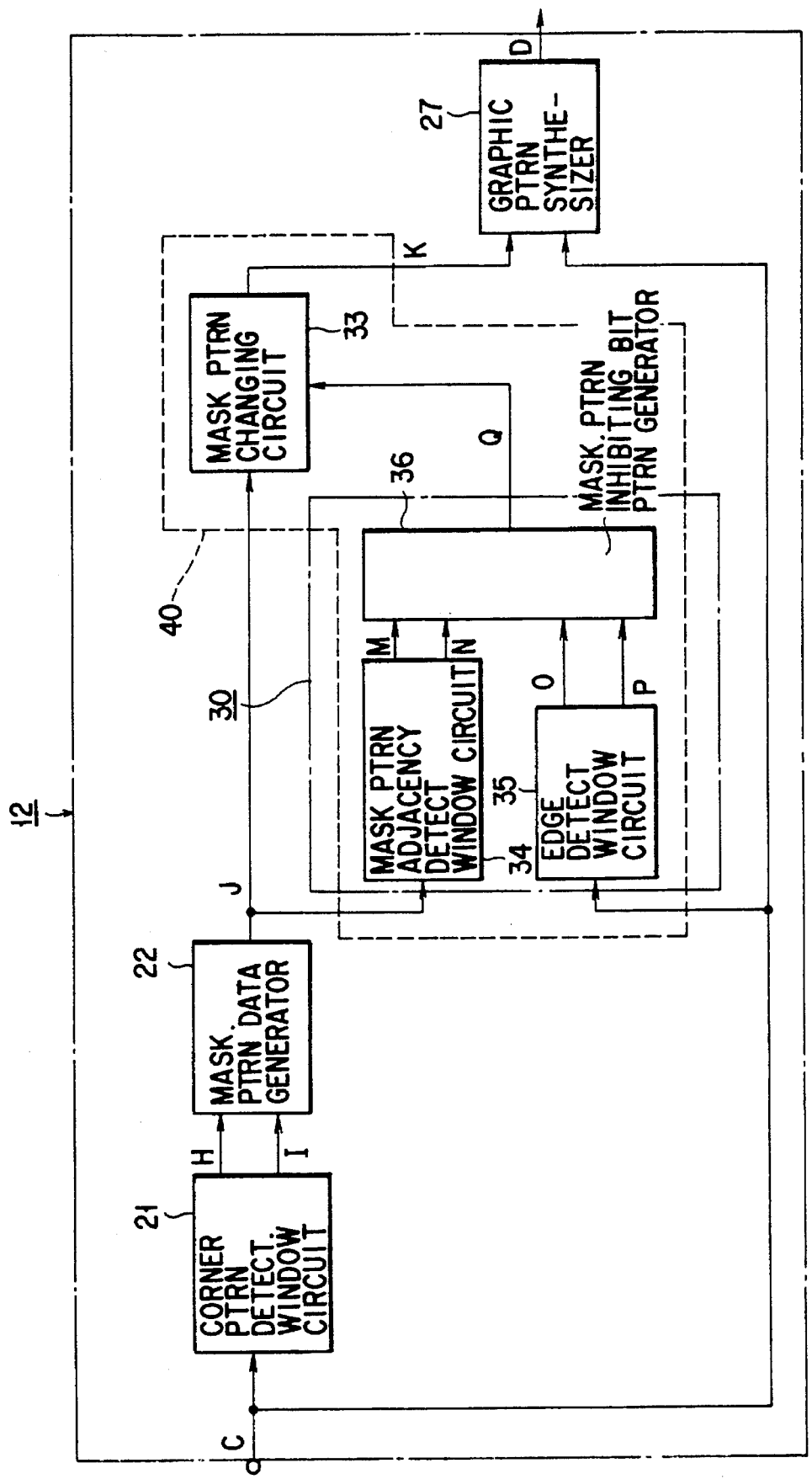
FIG. 28 is a block diagram showing the arrangement of a corner-rounded pattern correcting circuit.

FIG. 28 shows the arrangement of a corner-rounded pattern correcting circuit 40 and the manner in which the circuit 40 is arranged in a corner rounding circuit 12. The components enclosed with the dotted line in FIG. 28 constitute the corner-rounded pattern correcting circuit 40.

Every time masking pattern data J is input, a masking pattern adjacency detection window circuit 34 operates masking pattern adjacency detection templates shown at the right sides of FIGS. 25a to 25f. If one of the templates coincides with the input pattern, the circuit 34 sets a feature coincidence flag N together with a masking pattern code M indicating the corresponding masking pattern.

Every time a stripe pattern C is input, an edge detection window circuit 35 operates edge pattern detection templates shown at the left sides of FIGS. 25a to 25f. If one of the templates coincides with the input pattern, the circuit 35 sets a feature coincidence flag P together with an edge pattern code O indicating the corresponding edge pattern.

When the flags N and P are respectively set by the masking pattern adjacency detection window circuit 34 and the edge detection window circuit 35, a masking pattern inhibiting bit pattern generator 36 checks the masking pattern code M and the edge pattern code O. If the two codes are properly combined, the masking pattern inhibiting bit pattern generator 36 generates a masking pattern inhibiting bit pattern Q in accordance with the two inputs. In the masking pattern inhibiting bit pattern Q, data "0" are set at the positions of bits, in a masking pattern, which are to be inhibited, and data "1" are set at other positions.

In this case, an excessive rounding detector 30 is constituted by the masking pattern adjacency detection window circuit 34, the edge detection window circuit 35, and the masking pattern inhibiting bit pattern generator 36.

A masking pattern changing circuit 37 performs a logical product (AND) operation of the masking pattern data J, in which data "1" are set at the positions of bits, of stripe data, which are to be subjected to black and white inversion, and data "0" are set at other positions, and the masking pattern inhibiting bit pattern Q, in units of bits. That is, a masking pattern at a portion where the masking pattern inhibiting bit pattern Q is data "0" is removed. By supplying corrected masking pattern data K output from the masking pattern changing circuit 37, in place of the masking pattern data J, to a graphic pattern synthesizer 27, corner rounding results having no excessive rounding patterns can be obtained, as shown in FIGS. 26a to 26d and FIG. 27.

Figure 29:
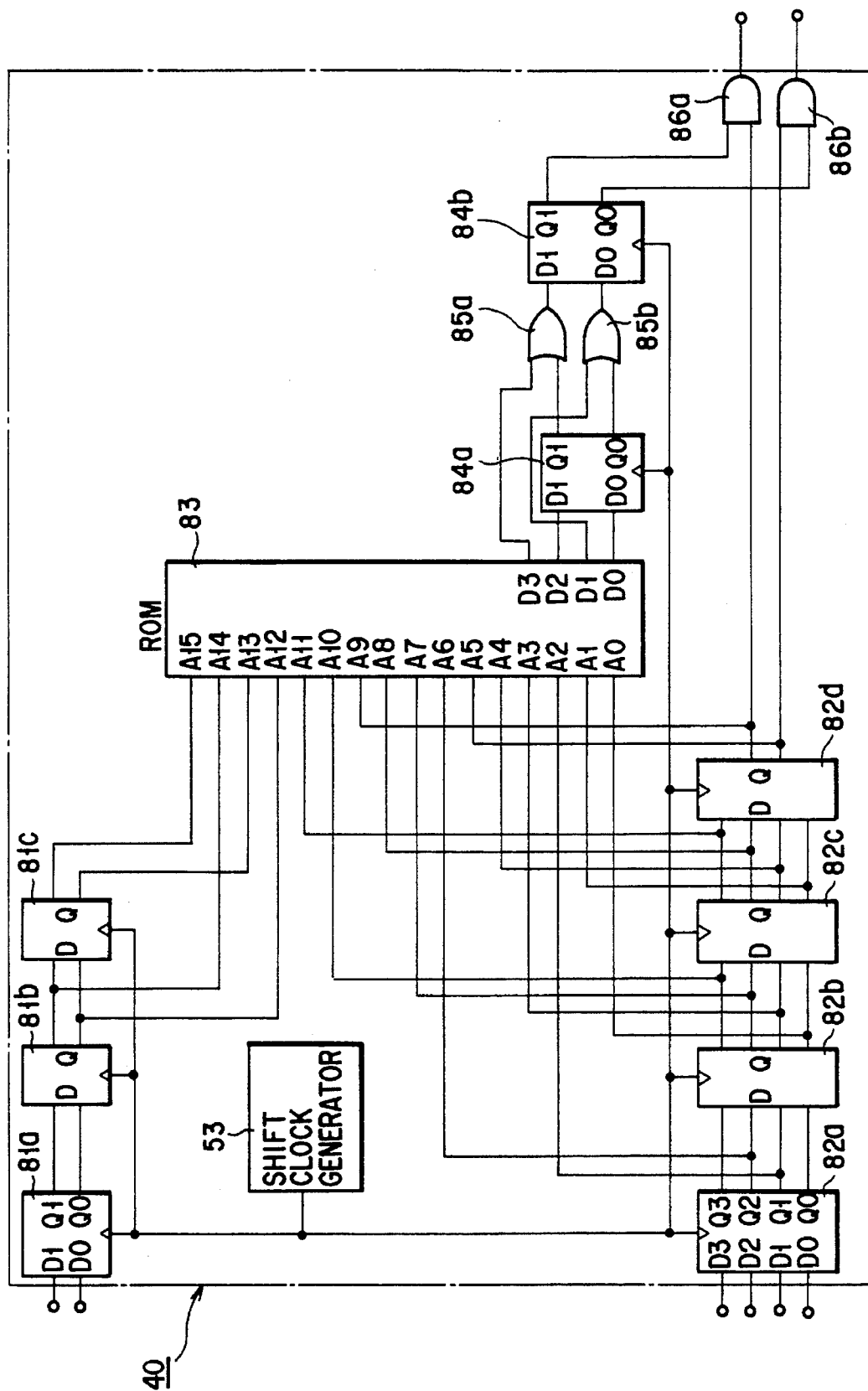
FIG. 29 is a circuit diagram showing the corner-rounded pattern correcting circuit in detail.

FIG. 29 shows a detailed circuit arrangement of the corner-rounded pattern correcting circuit 40 for correcting corner-rounded patterns in accordance with the concept shown in FIG. 28. As is apparent from FIG. 29, the corner-rounded pattern correcting circuit 40 is constituted by a shift clock generator 53, a masking latch group (81a to 81c), a stripe data latch group (82a to 82d), a ROM (Read Only Memory) 83, a masking pattern inhibiting bit pattern latch group (84a and 84b), OR gates (85a and 85b), and AND gates (86a and 86b).

The masking pattern adjacency detection window circuit 34 and the edge detection window circuit 35 in FIG. 28 must perform two-dimensional pattern matching. This function can be realized by various methods. In this case, however, only one case wherein a ROM is used as a table will be described. The masking pattern adjacency detection window circuit 34, the edge detection window circuit 35, and the masking pattern inhibiting bit pattern generator 36 simply output specific patterns with respect to specific input patterns, i.e., so-called table conversion. Therefore, these circuits can be integrated into a ROM having a sufficient capacity.

Since a masking pattern referred to by the masking pattern adjacency detection window circuit 34 consists of 12 bits, and stripe data referred to by the edge detection window circuit 35 consists of 4 bits, a total of 16 bits are required for an address input. In addition, since the masking pattern changing circuit 37 needs to inhibit an arbitrary pixel of four target masking pattern pixels, a 4-bit output is required. Therefore, these circuits can be realized by a ROM having a capacity of 64 Kbytes.

Figure 30A:
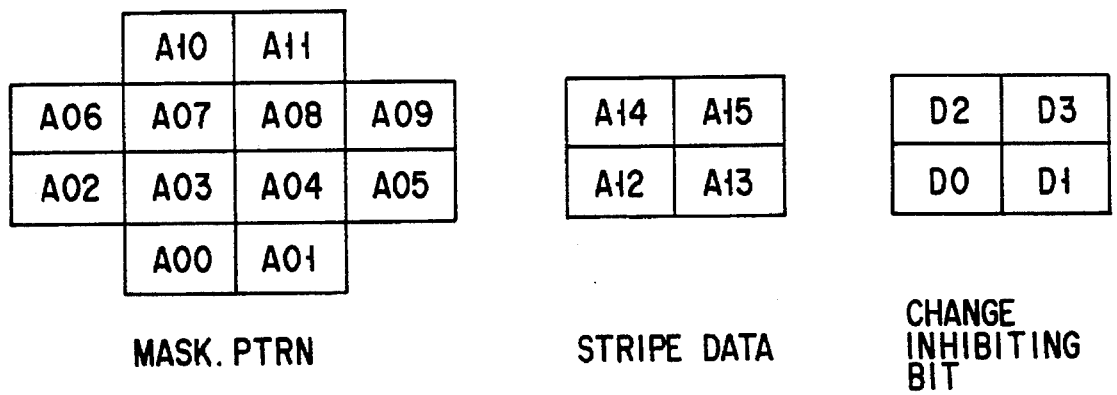
FIGS. 30a and 30b are views showing assignment of data to the addresses of a ROM and an example of data to be written.
Figure 30B:
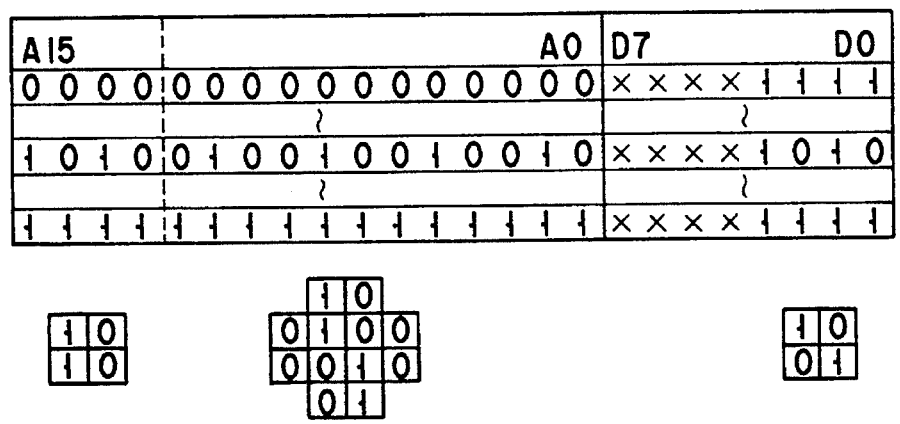

FIGS. 30a and 30b show data to be written in the ROM used in the arrangement shown in FIG. 29. FIG. 30a shows assignment of patterns, input to the masking pattern adjacency detection window circuit 34 and the edge detection window circuit 35, to ROM address bits, and assignment of a pattern, output from the masking pattern inhibiting bit pattern generator 36, to ROM data bits. White and black portions of stripe data are respectively represented by "0" and "1". The absence and presence of a masking pattern are respectively represented by "0" and "1". A change inhibiting pattern is expressed differently in a table and a chart. In a table, inhibition is represented by "0" ("1" in a bit pattern chart).

Referring to FIG. 29, when the stripe pattern data C and the masking pattern data J are sequentially supplied to a stripe pattern shift register constituted by the latches 81a to 81c driven by the shift clock generator 53 and to a masking pattern shift register constituted by the latches 82a to 82d, since the output terminals of the respective latches are connected to address input terminals A01 to A15 of the ROM 83 in accordance with the definitions shown in FIGS. 30a and 30b, the masking pattern adjacency detection window and the edge detection window are respectively scanned over the input patterns as the data are shifted. That is, since the bit patterns from the two windows are sequentially supplied to the input terminals of the ROM 83, the masking pattern inhibiting bit pattern Q sequentially appears at output terminals D0 to D3 of the ROM 83.

Although four masking pattern inhibiting bits simultaneously appear at the output terminals D0 to D3, they are temporarily held in a masking pattern inhibiting bit pattern shift register constituted by the latches 84a and 84b in order to match their timing with that of the original masking pattern in pipeline processing. Subsequently, the bits are input to the AND gates 86a and 86b having the function of the masking pattern changing circuit 33. More specifically, the outputs from the output terminal D1 and D3, which correspond to the right two bits of the masking pattern inhibiting bits, correspond to the output positions of the latch 82c, whereas the outputs from the output terminal D0 and D2, which correspond to the left two bits, correspond to the output positions of the latch 82b. Therefore, the outputs from the output terminals D1 and D3 are delayed by the latch 84b by one clock, and the outputs from the output terminals D0 and D2 are delayed by the latches 84a and 84b by two clocks. The delayed outputs are then input to the AND gates 86a and 86b. The OR gates 85a and 85b are required to correct adjacent input patterns which are independently detected during a scanning operation and require corner-rounded pattern correction processing.

The relationship between the corner-rounded pattern correcting circuit 40 and the corner rounding circuit 12 in the seventh embodiment will be described next. Although the corner-rounded pattern correcting circuit 40 is a component of the corner rounding circuit 12, the position of a corner pattern to be subjected to corner rounding processing in stripe data is indefinite. In n-bit corner rounding, a corner crossing stripes cannot be accurately processed by a corner pattern detection window unless bit pattern data extending outward from the stripe width by n bits is prepared, although it depends on the type of corner pattern to be detected/changed. For the same reason as described above, the corner-rounded pattern correcting circuit 40 requires masking pattern data extending outward from the stripe width by 2 bits and bit pattern data extending outward by 1 bit in order to perform corner-rounded pattern correction. Therefore, in order to properly perform corner rounding processing with a corner-rounded pattern correcting function with respect to an array of stripes each having a certain width, corner rounding circuits, each having a corner-rounded pattern correcting function in a width larger than the stripe width, must be arranged to be shifted from each other by 1 bit, and some of the previously processed stripes must be input again.

The embodiment incorporating these functions is shown in FIG. 19 described above. A portion of the stripe data (reference pattern data) C which has a predetermined width and is adjacent to the succeeding stripe is input to the stripe memory 24. The previous data having the predetermined width, stored in the stripe memory 24, is added to current data, and the resultant data is input to the corner pattern detection window circuit 21. The corner pattern detection window circuit 21, the masking pattern data generator 22, the masking pattern adjacency detection window circuit 34, the edge detection window circuit 35, the masking pattern inhibiting bit pattern generator 36, the masking pattern changing circuit 37, and the graphic pattern synthesizer 27 are formed into an array in a width obtained by adding the predetermined width to the stripe width. These circuits perform corner rounding processing and correction processing throughout a range equal to the data width of the stripe data C or more. In this case, in each component described above, a detecting/changing operation in the data width direction is performed while inaccurate portions are removed.

Figure 31:
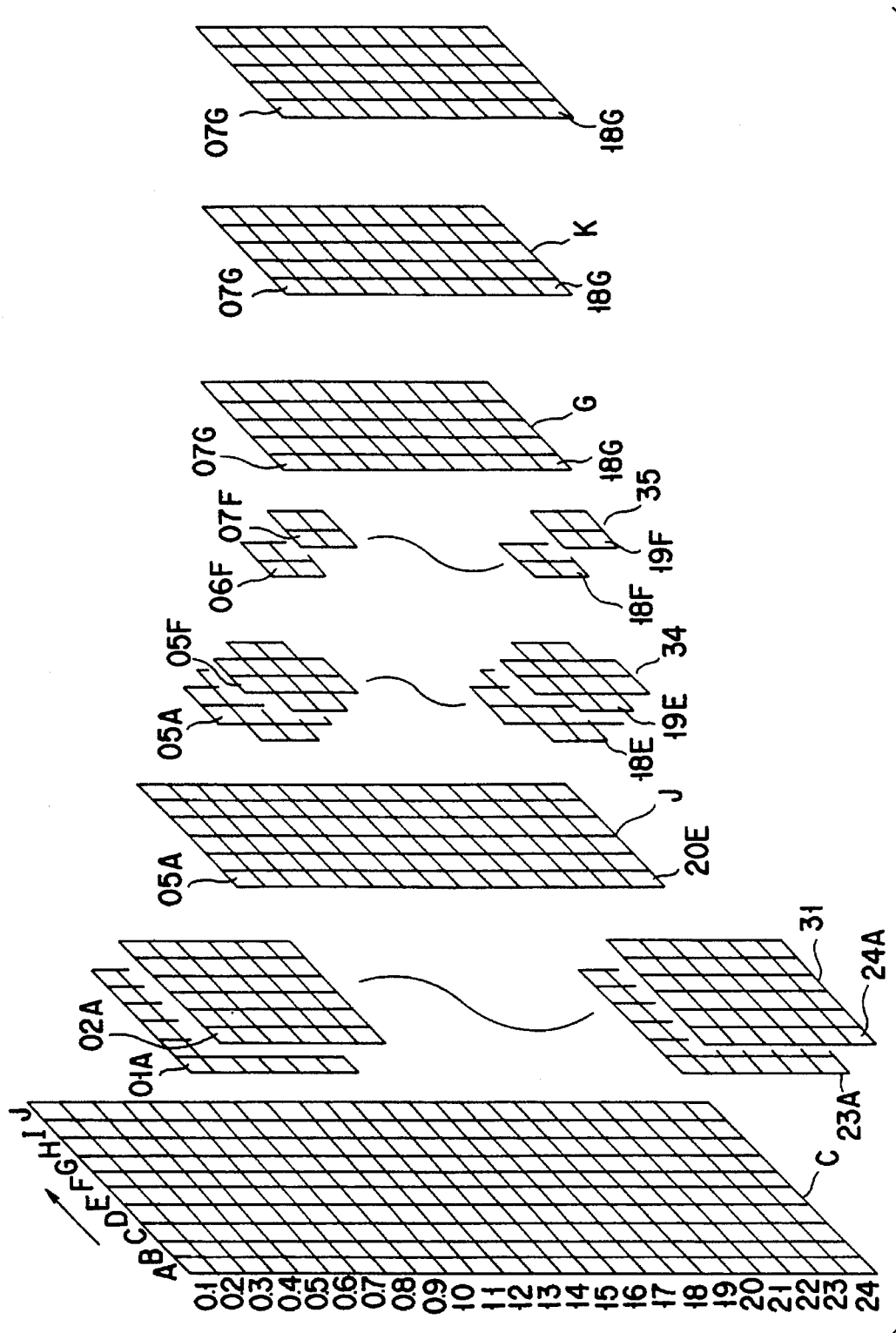
FIG. 31 is a view showing the relationship between stripe data, masking data, and a masking pattern inhibiting bit pattern.

FIG. 31 shows a state in which the respective windows are stacked on each other with reference to the addresses assigned in the width direction and shift direction of the stripe data C. In the corner pattern detection window circuit 21, the respective windows are stacked on each other while they are shifted from each other in the widthwise direction by 1 bit. Outputs from the respective windows are superposed on each other, and the OR signals of the superposed outputs are further superposed on each other in the shift direction to become the masking pattern data J. The masking pattern data J and the corresponding stripe data C are respectively processed by the masking pattern adjacency detection window circuit 34 and the edge detection window circuit 35 in the same manner, thus forming the masking pattern inhibiting bit pattern Q. The masking pattern inhibiting bit pattern Q and the masking pattern data J are ANDed to obtain the corrected masking pattern data K. The masking pattern data K and the stripe data C are exclusively ORed to obtain a final output from the corner rounding circuit.

As described above, according to the seventh embodiment, since the corner rounding circuit 12 performs corner rounding processing with respect to the reference pattern data C bit-developed by the bit development circuit 11, a reference pattern can be approximated to an actual test target pattern having rounded corners. Therefore, the threshold value range for comparison can be set to be narrower than that set in the conventional testing operation so that a defect near a corner, which cannot be detected by the conventional apparatus, can be detected. That is, a defect near a corner can be reliably detected without causing any pseudo-defect. Consequently, the pattern testing precision can be greatly improved.

Furthermore, in the seventh embodiment, the corner-rounded pattern correcting circuit 40 constituted by the excessive rounding detector (the circuits 34, 35, and 36) and the masking pattern changing circuit 33 is arranged in the corner rounding circuit 12. This arrangement prevents the generation of reference pattern data which is generated when the distance between the respective corners to be rounded is smaller than the size of a masking pattern and which cannot be obtained in an actual reticle manufacturing process. Therefore, defects even in more complicated patterns can be tested with high precision.

(Eighth Embodiment)

FIG. 32 is a block diagram showing the arrangement of a main part of a pattern testing apparatus according to the eighth embodiment of the present invention. The same reference numerals in FIG. 32 denote the same parts as in FIG. 19, and a detailed description thereof will be omitted.

The eighth embodiment is different from the seventh embodiment in that a masking pattern memory 39 is newly added. In the sixth embodiment, in order to obtain masking pattern data extending outward from the stripe width by 2 bits, which is required by the corner-rounded pattern correcting circuit 40, the data processing width of a corner pattern detection window circuit 21 and a masking pattern data generator 22 is set to be equal to the width required for processing stripe data or more so that the previous stripe data is processed again. In contrast to this, according to the eighth embodiment, as shown in FIG. 32, a portion of the previous stripe data which has a predetermined width is stored, and the masking pattern memory 39 for adding the data to current data is prepared. Therefore, the data processing width (parallel data processing amount) required for the corner pattern detection window circuit 21 and the masking pattern data generator 22 can be reduced.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A pattern inspection apparatus for comparing/collating test target pattern data obtained from a test target pattern with design pattern data of the pattern to detect the presence/absence of a defect which is present in a test target pattern, comprising:

pattern generating means for developing data of a design pattern corresponding to the test target pattern into bits, corner rounding means for performing corner rounding processing with respect to reference pattern data obtained by the pattern generating means, and comparing means for comparing second reference pattern data which is obtained by rounding the reference pattern data on the basis of the reference pattern data and a feature of the corresponding pattern, with the test pattern data obtained from the test target pattern, said corner rounding means including:

a corner pattern detector for scanning a corner pattern detection window having a predetermined range with respect to the reference pattern data, obtained by bit development performed by said pattern generating means, to extract a contour pattern in said window in the range, and detecting a corner pattern to be subjected to corner rounding processing in accordance with the extracted contour pattern, a masking pattern data generator for generating masking pattern data corresponding to the corner pattern detected by said corner pattern detector, and a graphic pattern synthesizing circuit for synthesizing graphic pattern data using the detected corner pattern in the reference pattern data with masking pattern data corresponding to the graphic pattern data, thereby rounding a corner portion of the reference pattern data;

wherein said comparing means compares the second reference pattern data, obtained by said graphic pattern synthesizing circuit, with the test pattern data using a predetermined threshold value level, said corner pattern detector comprises a contour portion determining circuit for scanning said corner pattern detection window to independently test a contour pattern in said window, and an internal portion determining circuit for independently testing an internal pattern in said window excluding the contour portion; and a logical operation is performed by said corner pattern detector on the basis of a test result obtained by said contour pattern determining circuit and a test result obtained by said internal portion determining circuit to test/determine whether the test target pattern data coincides with the reference pattern data.

2. A pattern inspection apparatus for comparing/collating test target pattern data obtained from a test target pattern with design pattern data of the pattern to detect the presence/absence of a defect which is present in a test target pattern, comprising:

pattern generating means for developing data of a design pattern corresponding to the test target pattern into bits, corner rounding means for performing corner rounding processing with respect to reference pattern data obtained by the pattern generating means, and comparing means for comparing second reference pattern data which is obtained by rounding the reference pattern data on the basis of the reference pattern data and a feature of the corresponding pattern, with the test pattern data obtained from the test target pattern, said corner rounding means including:

a corner pattern detector for scanning a corner pattern detection window having a predetermined range with respect to the reference pattern data, obtained by bit development performed by said pattern generating means, to extract a contour pattern in said window in the range, and detecting a corner pattern to be subjected to corner rounding processing in accordance with the extracted contour pattern, a masking pattern data generator for generating masking pattern data corresponding to the corner pattern detected by said corner pattern detector, and a graphic pattern synthesizing circuit for synthesizing graphic pattern data using the detected corner pattern in the reference pattern data with masking pattern data corresponding to the graphic pattern data, thereby rounding a corner portion of the reference pattern data;

wherein said masking pattern data generator comprises at least one storage table for storing/holding a plurality of pattern shapes as the masking pattern data, an arbitrary pattern shape is selected from said storage table in accordance with a command from a predetermined controller, and a rounded shape of a corner is changed in accordance with a selected arbitrary pattern shape.

3. The apparatus according to claim 2, wherein said corner pattern detector comprises:

a vertex determining section for testing bits located at predetermined four corners of a pattern in the range of said corner pattern detection window, a side determining section for testing a bit group corresponding to a side of the pattern, and a corner determining section for testing on the basis of test results obtained by said vertex determining section and said side determining section whether the pattern is a corner.

4. The apparatus according to claim 2, wherein said corner rounding means can change a maximum bit count of a mask for corner rounding processing by selectively switching a plurality of pattern detection window circuits, each of which defines a maximum bit count of a mask in advance, in accordance with a predetermined command from a predetermined controller.

5. The apparatus according to claim 2, wherein said corner rounding means further comprises a buffer circuit for temporarily storing a portion of said reference pattern data having a predetermined width as first stripe data the first stripe data being added to second stripe data subsequently input to said buffer circuit to form added stripe data which is input to said corner pattern detector.

6. A pattern inspection apparatus for comparing/collating test target pattern data obtained from a test target pattern with design pattern data of the pattern to detect the presence/absence of a defect which is present in a test target pattern, comprising:

pattern generating means for developing data of a design pattern corresponding to the test target pattern into bits, corner rounding means for performing corner rounding processing with respect to reference pattern data obtained by the pattern generating means, and comparing means for comparing second reference pattern data which is obtained by rounding the reference pattern data on the basis of the reference pattern data and a feature of the corresponding pattern, with the test pattern data obtained from the test target pattern, said corner rounding means including:

a corner pattern detector for scanning a corner pattern detection window having a predetermined range with respect to the reference pattern data, obtained by bit development performed by said pattern generating means, to extract a contour pattern in said window in the range, and detecting a corner pattern to be subjected to corner rounding processing in accordance with the extracted contour pattern, a masking pattern data generator for generating masking pattern data corresponding to the corner pattern detected by said corner pattern detector, and a graphic pattern synthesizing circuit for synthesizing graphic pattern data using the detected corner pattern in the reference pattern data with masking pattern data corresponding to the graphic pattern data, thereby rounding a corner portion of the reference pattern data;

wherein said corner pattern detector comprises a first latch group having a function of latching said reference pattern data, and a memory connected to said first latch group and having a function of storing masking pattern data, said masking pattern data generator comprises said memory having the function of storing masking pattern data, a second latch group connected to said memory and having a function of latching output data from said memory, and an OR gate group connected to said memory and said second latch group, and said graphic pattern synthesizing circuit comprises an exclusive-OR gate group.

7. A pattern inspection apparatus comprising:

bit pattern generating means for generating reference pattern data by bit development of a design pattern into bits;

corner rounding means for selecting a corner portion of said reference pattern data obtained by bit development performed by said bit pattern generating means, and performing corner rounding processing with respect to the corner portion to generate corner-rounded data; and comparing means for comparing said corner-rounded data obtained by rounding processing with test pattern data of a test target pattern, said corner rounding means including a corner pattern detector for detecting a corner pattern by scanning a corner pattern detection window with respect to the reference pattern data, a masking pattern data generator for generating masking pattern data corresponding to the corner pattern detected by said corner pattern detector, and a graphic pattern synthesizing circuit for synthesizing graphic pattern data including the detected corner pattern in the reference pattern data with masking pattern data corresponding to the graphic pattern data, thereby rounding a corner portion of the reference pattern data, and said pattern inspection apparatus further comprising:

corner-rounded pattern correcting means constituted by an excessive rounding detector for detecting an excessive rounding state, which is caused when corner rounding processing is performed with respect to a plurality of adjacent corners, by scanning the reference pattern data and corresponding masking pattern data, and a masking pattern changing circuit for changing a masking pattern in accordance with a test result obtained by said excessive rounding detector.

8. The apparatus according to claim 7, wherein said excessive rounding detector comprises:

a masking pattern adjacency detection window circuit for scanning a window with respect to a masking pattern corresponding to the reference pattern data to detect a position adjacent to the masking pattern, thereby detecting adjacency and a type of adjacency of the masking pattern, an edge detection window circuit for detecting an edge by scanning an edge detection window having a predetermined range with respect to reference pattern data input from said bit pattern generating means, and a masking pattern inhibiting bit pattern generator connected to said masking pattern adjacency detection window circuit and said edge detection window circuit for generating a masking pattern inhibiting bit pattern in accordance with a test result from said excessive rounding detector, and said masking pattern changing circuit changes the masking pattern into a predetermined masking pattern by removing partial masking pattern data in which the masking pattern inhibiting bit pattern generated by said masking pattern inhibiting bit pattern generator is present.

9. The apparatus according to claim 8, wherein said masking pattern changing circuit performs table conversion by using a memory which outputs said predetermined masking pattern based upon said masking pattern being input to said masking pattern changing circuit.

10. The apparatus according to claim 8, further comprising a masking pattern memory connected to said masking pattern adjacency detection window circuit and said masking data pattern generator for storing masking pattern data having a predetermined width, said masking pattern data and a succeeding stripe data of current first masking pattern data being consecutively input to said excessive rounding detector, and means for adding the first masking pattern data having the predetermined width stored in said masking pattern memory to subsequently input second masking pattern data to obtain resultant data, wherein the resultant data is input to said excessive rounding detector.

11. The apparatus according to claim 7, further comprising a stripe memory for storing stripe data, required for said corner rounding means and a distribution function calculator, and wherein said distribution function calculator performs weighting/addition and multivalue conversion of the design data by using a point spread function representing a resolution of a predetermined testing optical system, thereby forming desired reference data.

12. The apparatus according to claim 11, wherein said stripe memory stores stripe data having a predetermined width, as first stripe data which is adjacent to subsequently input second stripe data of consecutively input reference pattern data, said apparatus further comprising:

means for adding first stripe data having the predetermined width stored in said stripe memory to the second stripe data to obtain resultant data, and inputting the resultant data to said corner pattern detector wherein first data from said masking pattern data generator, second data from said pattern correcting means, and third data from said graphic pattern synthesizing circuit are arranged into an array having a width obtained by adding a predetermined width to a width of said first, second and third data, and corner rounding processing and correction processing is performed throughout a range not less than a data width of the stripe data.

13. The apparatus according to claim 7, wherein said excessive rounding detector comprises:

a masking pattern adjacency detection window circuit which detects, every time masking pattern data is input, by using a masking pattern adjacency detection template, whether the template coincides with input pattern, and sets a masking pattern code indicating the masking pattern coinciding with the template, and a first flag indicating coincidence, if the template and the input pattern coincide with each other, an edge detection window circuit which detects, every time a stripe pattern is input, by using an edge pattern detection template, whether the template coincides with the input pattern, and sets an edge pattern code indicating the edge pattern coinciding with the template, and a second flag indicating coincidence, if the template and the input pattern coincide with each other, and a masking pattern inhibiting bit pattern generator which tests the masking pattern code and the edge pattern code when the first flag and the second flag are set, and generates a masking pattern inhibiting bit pattern in accordance with the masking pattern and edge pattern codes if the masking pattern and edge pattern codes constitute a predetermined combination, the masking pattern inhibiting bit pattern comprising first type data indicating positions of bits to be inhibited, in the masking patterns, and second type data indicating other positions of bits.

14. The apparatus according to claim 7, wherein said corner-rounded pattern correcting means comprises:

a masking latch group serving as a masking pattern shift register, a stripe data latch group serving as a stripe pattern shift register, a shift clock generator, connected to said latch groups, for driving said latch groups, a ROM for generating a masking pattern inhibiting bit pattern on the basis of bit pattern data supplied from each of said latch groups, a masking pattern inhibiting bit pattern latch group, connected to output of said ROM, serving as a second masking pattern shift register for temporarily holding the masking pattern inhibiting bit pattern to cause the bit pattern to synchronize with an original masking pattern, an OR gate group connected to said inhibiting bit pattern latch group in a predetermined manner for performing predetermined correction processing with respect to an input pattern which requires corner-rounded pattern correction of adjacent corners which are separately detected, and an AND gate group, connected to said inhibiting bit pattern latch group, for further performing predetermined correction processing with respect to the corrected pattern.

* * * * *